US012704521B2

(12) United States Patent
Lee et al.

(10) Patent No.: US 12,704,521 B2
(45) Date of Patent: Aug. 11, 2026

(54) ON-SITE RAPID QUANTIFICATION OF TETRAHYDROCANNABINOL

(71) Applicants: The General Hospital Corporation, Boston, MA (US); INDUSTRY-ACADEMIC COOPERATION FOUNDATION, YONSEI UNIVERSITY, Seoul (KR); Institute for Basic Science, Daejeon (KR)

(72) Inventors: Hakho Lee, Acton, MA (US); Ralph Weissleder, Peabody, MA (US); Hojeong Yu, Seoul (KR); Jinwoo Cheon, Seoul (KR)

(73) Assignees: The General Hospital Corporation, Boston, MA (US); Industry-Academic Cooperation Foundation, Yonsei University, Seoul (KR); Institute For Basic Science, Daejeon (KR)

( * ) Notice: Subject to any disclaimer, the term of this patent is extended or adjusted under 35 U.S.C. 154(b) by 780 days.

(21) Appl. No.: 18/017,546

(22) PCT Filed: Jul. 26, 2021

(86) PCT No.: PCT/US2021/043234

§ 371 (c)(1),
(2) Date: Jan. 23, 2023

(87) PCT Pub. No.: WO2022/020814

PCT Pub. Date: Jan. 27, 2022

(65) Prior Publication Data

US 2023/0266348 A1 Aug. 24, 2023

Related U.S. Application Data

(60) Provisional application No. 63/056,216, filed on Jul. 24, 2020.

(51) Int. Cl.
*G01N 33/94* (2006.01)
*G01N 33/543* (2006.01)
*A61B 10/00* (2006.01)

(52) U.S. Cl.
CPC ..... *G01N 33/948* (2013.01); *G01N 33/54366* (2013.01); *A61B 2010/0009* (2013.01); *A61B 10/0051* (2013.01)

(58) Field of Classification Search
CPC ........... G01N 33/948; G01N 33/54366; G01N 33/487; A61B 10/0051; A61B 2010/0009;
(Continued)

(56) References Cited

U.S. PATENT DOCUMENTS 7,029,627 B2 4/2006 Alley
10,035,146 B2 7/2018 Fuller et al.
(Continued)

FOREIGN PATENT DOCUMENTS

WO WO 2019/018697 1/2019

OTHER PUBLICATIONS

Anizan et al., "Oral fluid cannabinoid concentrations following controlled smoked cannabis in chronic frequent and occasional smokers," Anal Bioanal Chem, Oct. 2013, 405(26):8451-8461.
(Continued)

*Primary Examiner* — Samuel P Siefke
(74) *Attorney, Agent, or Firm* — Fish & Richardson P.C.

(57) ABSTRACT

Aspects of the present disclosure provide devices and methods for rapid, quantitative, on-site detection of controlled substances. Devices include a sample processing module and a sensor cartridge, and optionally a detection cradle.

27 Claims, 29 Drawing Sheets

(58) Field of Classification Search
CPC ....... B01L 2200/0605; B01L 2300/042; B01L 2300/046; B01L 2300/0663; B01L 2300/0681; B01L 2300/0867; B01L 2300/0896; B01L 2400/0478; B01L 2400/0644; B01L 3/50273
See application file for complete search history.

(56) References Cited

U.S. PATENT DOCUMENTS

| | | | |
|---|---|---|---|
| 2007/0128070 | A1 | 6/2007 | Wu et al. |
| 2014/0134073 | A1 | 5/2014 | Fuller et al. |
| 2015/0182156 | A1 | 7/2015 | Engbersen et al. |
| 2016/0263577 | A1 | 9/2016 | Ismagilov et al. |
| 2018/0304260 | A1* | 10/2018 | Thomas ............ B01L 3/502761 |
| 2019/0187162 | A1* | 6/2019 | Shastry .................. G01N 21/13 |
| 2019/0366326 | A1 | 12/2019 | Volland |
| 2020/0147605 | A1 | 5/2020 | Donaldson et al. |

OTHER PUBLICATIONS

Bosker and Huestis, “Oral fluid testing for drugs of abuse,” Clin Chem, Nov. 2009, 55(11):1910-1931.
Breidi et al., “Enzymatic digestion and selective quantification of underivatised delta-9-tetrahydrocannabinol and cocaine in human hair using gas chromatography-mass spectrometry,” J. Anal. Methods Chem., 2012, 2012:907893, 7 pages.
Brown et al., “Trends in Marijuana Use Among Pregnant and Nonpregnant Reproductive-Aged Women, 2002-2014,” JAMA, Jan. 2017, 317(2):207-209, 3 pages.
Casajuana Köguel et al., “Psychoactive constituents of cannabis and their clinical implications: a systematic review,” Adicciones, Apr. 2018, 30(2):140-151.
Cerdá et al., “Association between recreational marijuana legalization in the United States and changes in marijuana use and cannabis use disorder from 2008 to 2016,” JAMA Psychiatry, Feb. 2020, 77(2):165-171.
Cirimele et al., “Oral fluid testing for cannabis: on-site Oraline® IV s.a.t. device versus GC/MS,” Forensic Sci. Int., Sep. 2006, 161(2-3):180-184, 5 pages.
Coleman et al., “High-efficiency electrokinetic micromixing through symmetric sequential injection and expansion,” Lab on a Chip, Aug. 2006, 6(8):1033-1039.
Dahlgren et al., “Recreational cannabis use impairs driving performance in the absence of acute intoxication,” Drug and Alcohol Dependence, Mar. 2020, 208:107771, 10 pages.
Dai et al., “A National Survey of Marijuana Use Among US Adults With Medical Conditions, 2016-2017,” JAMA Netw Open, Sep. 2019, 2(9):e1911936, 13 pages.
Desrosiers and Huestis, “Oral fluid drug testing: Analytical approaches, issues and interpretation of results,” J Anal Toxicol, Jul. 2019, 43(6):415-443.
Desrosiers et al., “Phase I and II cannabinoid disposition in blood and plasma of occasional and frequent smokers following controlled smoked cannabis,” Clin Chem, Apr. 2014, 60(4):631-643, 13 pages.
Desrosiers et al., “Smoked cannabis' psychomotor and neurocognitive effects in occasional and frequent smokers,” J Anal Toxicol, May 2015, 39(4):251-261.
Drummer, “Drug testing in oral fluid,” Clin Biochem Rev, Aug. 2006, 27(3):147-159.
Fergusson et al., “Is driving under the influence of cannabis becoming a greater risk to driver safety than drink driving? Findings from a longitudinal study,” Accid. Anal. Prev., Jul. 2008, 40(4):1345-1350.
Gill et al., “Selective sensing of THC and related metabolites in biofluids by host:guest arrays,” Chem Commun (Camb), Apr. 2020, 56(31):4352-4355, 5 pages.
Hall and Degenhardt, “Adverse health effects of non-medical cannabis use,” Lancet, Oct. 2009, 374(9698):1383-1391.
Hartley et al., “Effect of smoked cannabis on vigilance and accident risk using simulated driving in occasional and chronic users and the pharmacokinetic-pharmacodynamic relationship,” Clin. Chem., May 2019, 65(5):684-693.
Hartman and Huestis, “Cannabis effects on driving skills,” Clin Chem, Mar. 2013, 59(3):478-492.
Hasin et al., “US adult illicit cannabis use, cannabis use disorder, and medical marijuana laws: 1991-1992 to 2012-2013,” JAMA Psychiatry, Jun. 2017, 74(6):579-588, 10 pages.
Hu et al., “Oligonucleotide-linked gold nanoparticle aggregates for enhanced sensitivity in lateral flow assays,” Lab Chip, Nov. 2013, 13(22):4352-4357.
International Preliminary Report on Patentability in International Appln. No. PCT/US2021/043234, mailed on Feb. 2, 2023, 7 pages.
International Search Report and Written Opinion in International Appln. No. PCT/US2021/043234, mailed on Nov. 2, 2021, 9 pages.
Jaeger, “Digit symbol substitution test: The case for sensitivity over specificity in neuropsychological testing,” J. Clin. Psychopharmacol., Oct. 2018, 38(5):513-519.
Jain et al., “Calculated absorption and scattering properties of gold nanoparticles of different size, shape, and composition: applications in biological imaging and biomedicine, ” J Phys Chem B, Mar. 2006, 110(14):7238-7248.
Katz-Talmor et al., “Cannabinoids for the treatment of rheumatic diseases—where do we stand?,” Nat. Rev. Rheumatol., 2018, 14:488-498, 11 pages.
Kauert et al., “Pharmacokinetic Properties of $\Delta^9$-Tetrahydrocannabinol in Serum and Oral Fluid,” J. Anal. Toxicol., Jun. 2007, 31(5):288-293.
Kubelka, “New contributions to the optics of intensely light-scattering materials,” J Opt Soc Am, May 1948, 38(5):448-457.
Lee and Huestis, “Current knowledge on cannabinoids in oral fluid,” Drug Test. Anal., Jan.-Feb. 2014, 6(1-2):88-111.
Lee et al., “Oral fluid cannabinoids in chronic, daily cannabis smokers during sustained, monitored abstinence,” Clin Chem, Aug. 2011, 57(8):1127-1136.
Lee et al., “Small molecule detection in saliva facilitates portable tests of marijuana abuse,” Analytical Chemistry, Aug. 2016, 88(15):7457-7461.
Meier et al., “Cannabis concentrate use in adolescents,” Pediatrics, Sep. 2019, 144(3):e20190338, 12 pages.
Milman et al., “Cannabinoids and metabolites in expectorated oral fluid following controlled smoked cannabis,” Clin Chim Acta, Apr. 2012, 413(7-8):765-770.
Milman et al., “Oral fluid and plasma cannabinoid ratios after around-the-clock controlled oral $\Delta^9$-etrahydrocannabinol administration,” Clin Chem, Nov. 2011, 57(11):1597-1606.
Mishra et al., “Simultaneous detection of salivary $\Delta^9$-tetrahydrocannabinol and alcohol using a Wearable Electrochemical Ring Sensor,” Talanta, May 2020, 211:120757, 8 pages.
Moore et al., “Cannabis use and risk of psychotic or affective mental health outcomes: a systematic review,” Lancet, Jul. 2007, 370(9584):319-328.
Morita et al., “Antibody fragments for on-site testing of cannabinoids generated via in vitro affinity maturation,” Biol Pharm Bull, 2017, 40(2):174-181.
Murray et al., “Cannabis, the mind and society: the hash realities,” Nature Reviews Neuroscience, Nov. 2007, 8(11):885-895.
Parekh et al., “Marijuana Use Among Young Adults (18-44 Years of Age) and Risk of Stroke: A Behavioral Risk Factor Surveillance System Survey Analysis,” Stroke, Jan. 2020, 51(1):308-310, 6 pages.
Pham et al., “Smartphone-based symbol-digit modalities test reliably captures brain damage in multiple sclerosis,” npj Digital Medicine, Feb. 2021, 4:36, 13 pages.
Plevniak et al., “3D printed auto-mixing chip enables rapid smartphone diagnosis of anemia,” Biomicrofluidics, Oct. 2016, 10(5):054113, 11 pages.
Prashad and Filbey, “Cognitive motor deficits in cannabis users,” Curr Opin Behav Sci, Feb. 2017, 13:1-7.
Rogeberg and Elvik, “The effects of cannabis intoxication on motor vehicle collision revisited and revised,” Addiction, Aug. 2016, 111(8):1348-1359.

(56) References Cited

OTHER PUBLICATIONS

Röhrich et al., "Concentrations of $\Delta^9$-tetrahydrocannabinol and 11-nor-9-carboxytetrahydrocannabinol in blood and urine after passive exposure to cannabis smoke in a coffee shop," J. Anal. Toxicol., May 2010, 34(4):196-203.

Samhsa.gov [online], "Key substance use and mental health indicators in the United States: Results from the 2018 national survey on drug use and health," 2019, retrieved on Mar. 29, 2023, retrieved from URL<https://www.samhsa.gov/data/sites/default/files/reports/rpt35319/2020NSDUHFFR102121.htm>, 173 pages.

Squires et al., "Making it stick: convection, reaction and diffusion in surface-based biosensors," Nat Biotechnol, Apr. 2008, 26(4):417-426.

Stevenson et al., "Rapid Response Electrochemical Biosensor for Detecting Thc In Saliva," Sci Rep, Sep. 2019, 9(1):12701, 11 pages.

Swanson et al., "Rapid light transmittance measurements in paper-based microfluidic devices," Sens Biosensing Res, Sep. 2015, 5:55-61.

Swortwood et al., "Cannabinoid disposition in oral fluid after controlled smoked, vaporized, and oral cannabis administration," Drug Test. Anal., Jun. 2017, 9(6):905-915.

Toennes et al., "Pharmacokinetic properties of $\Delta^9$-tetrahydrocannabinol in oral fluid of occasional and chronic users," J. Anal. Toxicol., May 2010, 34(4):216-221.

Veldstra et al., "Comparing treatment effects of oral THC on simulated and on-the-road driving performance: testing the validity of driving simulator drug research," Psychopharmacology, Aug. 2015, 232(16):2911-2919.

Verstraete, "Detection times of drugs of abuse in blood, urine, and oral fluid," Therapeutic Drug Monitoring, Apr. 2004, 26(2):200-205.

Wang et al., "Angle dependent light scattering by gold nanospheres," J Phys Conf Ser, 2016, 682:012018, 6 pages.

Wanklyn et al., "Disposable screen printed sensor for the electrochemical detection of delta-9-tetrahydrocannabinol in undiluted saliva," Chem Cent J, Jan. 2016, 10:1, 11 pages.

wdr.unodc.org [online], "World Drug Report 2019: 35 million people worldwide suffer from drug use disorders while only 1 in 7 people receive treatment," Jun. 21, 2019, retrieved on May 9, 2023, retrieved from URL<https://wdr.unodc.org/wdr2019/press/WDR_2019_press release.pdf>, 2 pages.

Wong et al., "Diffusion of gold nanoparticles in toluene and water as seen by dynamic light scattering," J Nanopart Res, Mar. 2015, 17:153, 8 pages.

Yang et al., "Gold nanocage-based lateral flow immunoassay for immunoglobulin G," HHS Public Access Author Manuscript, doi: 10.1007/s00604-017-2176-5, published online Nov. 27, 2017; published in final edited form as: Mikrochim Acta, Jul. 2017, 184(7):2023-2029, 16 pages.

Yu et al., "A rapid assay provides on-site quantification of tetrahydrocannabinol in oral fluid," HHS Public Access Author Manuscript, doi: 10.1126/scitranslmed.abe2352, published online May 23, 2022; published in final edited form as: Sci Transl Med., Oct. 2021, 13(616):eabe2352, 21 pages.

Extended European Search Report in European Appln. No. 21846591.2, dated Jul. 26, 2024, 7 pages.

* cited by examiner

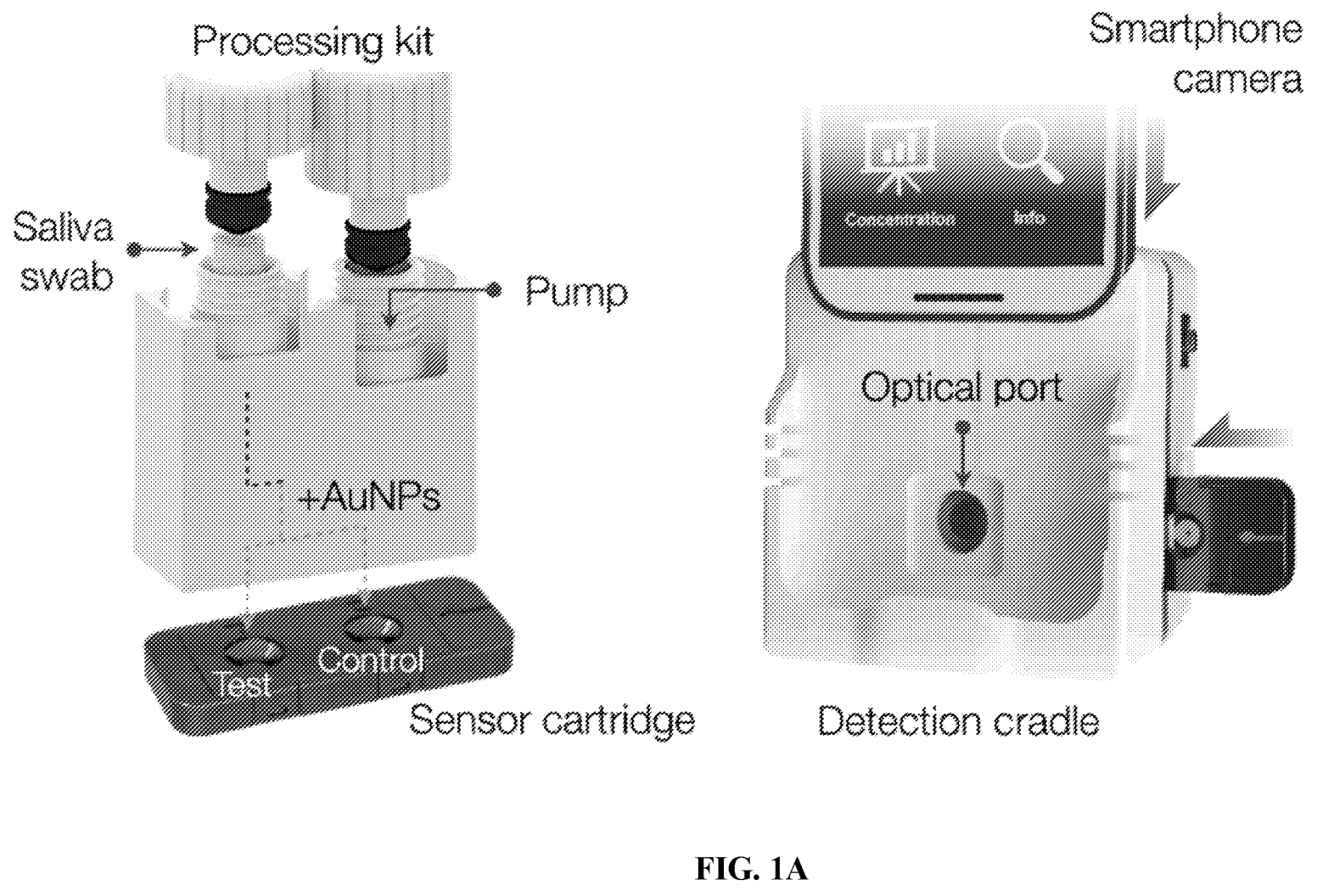

Smartphone camera

Optical port

Detection cradle

Processing kit

Saliva swab

Pump

+AuNPs

Sensor cartridge

Test

Control

FIG. 1A

[THC] (ng/mL)
$10^6$
$10^4$
$10^2$
$10^0$
0
Cannabis users
Controls
Edible ($n$ = 3)
Cannabis smoker ($n$ = 40)
Tobacco ($n$ = 13)
Non-smoker ($n$ = 30)

(i) During saliva collection

| | |
|---|---|
| Overflow | connected |
| Saliva outlet | closed |
| Saliva inlet | closed |
| Air channe | closed |

(ii). After saliva collection

| | | |
|---|---|---|
| Overflow | closed | |
| Saliva outlet | open | connected |
| Saliva inlet | open | connected |
| Air channe | open | |

ON-SITE RAPID QUANTIFICATION OF TETRAHYDROCANNABINOL

CLAIM OF PRIORITY

This application is a U.S. National Phase Application under 35 U.S.C. § 371 of International Patent Application No. PCT/US2021/043234, filed on Jul. 26, 2021, which claims the benefit of U.S. Provisional Patent Application No. 63/056,216, filed on Jul. 24, 2020, which is incorporated by reference herein in its entirety.

FIELD

The subject matter disclosed herein generally relates to devices and methods for detection of a controlled substance such as tetrahydrocannabinol (THC).

BACKGROUND

*Cannabis* is a commonly used psychoactive drug with an estimated 180 million users worldwide. In the US, the user number exceeds 24 millions[1]; the proportion of daily or near-daily users (>40%) is on the rise, spurred by the legalization of *cannabis* for recreational and medicinal use. Despite its therapeutic and recreational "high" effects, there are increasing public health concerns for users operating machinery and driving under the influence. Inhaled through smoking or vaping, $\Delta^9$-tetrahydrocannabinol (THC), rapidly enters the circulation and reaches the brain. Acute psychological effect set in within minutes and lasts for two to four hours[2,3]. Driving motor vehicles during this period should be avoided, as persons' cognitive (e.g., decision making, concentration) and motor (e.g., reaction time, coordination) functions are compromised[4-7]. Several epidemiological studies found an increased accident risk associated with *cannabis* uses[8-10].

SUMMARY OF THE INVENTION

The present disclosure is based, at least in part, on the development of methods and devices for detection of a controlled substance such as THC that provide several advantages over conventional approaches. Such advantages can include:

(a) Increased assay speed, which can be achieved, at least in part, from higher flow rates obtained using a cartridge design that includes a disk-shaped membrane. For example, using methods and devices described herein, assay results can be obtained within 5 minutes including sample collection.

(b) Increased assay sensitivity, which can be achieved, at least in part, from concentration of input samples into a small sensing area achieved using a cartridge design that includes a disk-shaped membrane covered by a sealing film with a hole for receiving the sample.

(c) Increased reproducibility and quantification, which can be achieved, at least in part, from using optical transmission that detects higher analytical signals than a conventional reflection mode.

(d) Simplified sample handling, which can be achieved with easy-to-use premade sample processing kits and sensor cartridges.

(e) Simplified design that is adaptable for detection of a wide range of controlled substances.

Accordingly, aspects of the present disclosure provide devices and methods for rapid and quantitative detection of a controlled substance (e.g., THC) in a sample (e.g., a saliva sample).

THC, the primary psychoactive ingredient of *cannabis*, impairs cognitive and motor function in a concentration-dependent fashion. While drug testing is commonly performed for employment and law enforcement purposes, available tests either produce low-sensitive binary results (e.g., lateral flow assays) or have a long turnaround (e.g., gas chromatography-mass spectrometry). To enable on-site THC quantification in minutes, a rapid assay for oral THC analysis was developed (one example of which is referred to herein as EPOCH, express probe for on-site *cannabis* inhalation). In some embodiments, EPOCH features a distinctive sensor design (e.g., a radial membrane, transmission optics) contained in a compact cartridge. This integrated approach permitted assay completion within 5 minutes with a detection limit of 0.17 ng/mL THC, which is below the regulatory guideline (1 ng/mL). As a proof of concept for field testing, the exemplary EPOCH method was applied to assess oral fluid samples from *cannabis* users (n=43) and controls (n=43). The exemplary EPOCH method detected oral THC in all specimens from *cannabis* smokers (median concentration, 478 ng/mL) and THC-infused food consumers. Intriguingly, longitudinal monitoring showed a fast drop in THC levels within the first 6 hours of *cannabis* smoking (half-life, 1.4 hrs).

In some embodiments, a device for detecting a controlled substance comprises (a) a sample processing module comprising a metering reservoir reversibly connected to a sample chamber, an air chamber, and a loading chamber via a first fluidic channel, a second fluidic channel, and a third fluidic channel, respectively, wherein the metering reservoir is reversibly connected to a waste chamber via a syphon that is configured to actuate upon a predetermined volume of liquid being received in the metering reservoir, wherein the loading chamber comprises a detection probe that binds a controlled substance, and wherein the loading chamber is connected to a fourth fluidic channel comprising one or more openings; (b) a sensor cartridge comprising a control membrane aligned to the control sample outlet and comprising a loading control probe that binds to the detection probe, and a test membrane aligned to the test sample outlet and comprising a capture probe comprising the controlled substance; and (c) a first cap having a protrusion that forms a piston relative to the sample chamber when the first cap is joined to the sample chamber, and a second cap having a protrusion that forms a piston relative to the air chamber when the second cap is joined to the air chamber.

In some embodiments, the metering reservoir is positionable in a first position where the metering reservoir is aligned with the first fluidic channel to allow fluid to flow from the sample chamber to the metering reservoir.

In some embodiments, the metering reservoir is positionable in a second position where the metering reservoir is aligned with the second fluidic channel to allow air to flow from the air chamber to the metering reservoir, and where the metering reservoir is aligned with the third fluidic channel to allow fluid to flow from the metering reservoir to the loading chamber.

In some embodiments, the reservoir has a sample volume of 5 to 50 μL. In some embodiments, the reservoir has a sample volume of 15 to 25 μL.

In some embodiments, the first fluidic channel comprises a filter between the sample chamber and the metering reservoir.

In some embodiments, the fourth fluidic channel comprising a microfluidic mixer.

In some embodiments, the detection probe is conjugated to a detectable label.

In some embodiments, the control membrane and the test membrane are disk shaped.

In some embodiments, the control membrane and the test membrane are laminated.

In some embodiments, the loading control probe and the capture probe are immobilized at the center of the control membrane and test membrane, respectively.

In some embodiments, the sensor cartridge is detachable from the sample processing module. In some embodiments, the sensor cartridge comprises a housing.

In some embodiments, the sample processing module comprises circumferential screw threads, and the first cap and the second cap comprise circumferential receiving threads.

In some embodiments, devices described herein further comprise a detection cradle comprising a light source and a lens.

Aspects of the present disclosure provide methods of detecting a controlled substance in a saliva sample from a subject comprising (a) collecting a saliva sample from a subject using an oral swab, (b) loading the oral swab into the sample processing module of any of the devices described herein, (c) engaging the first cap with the sample chamber and the second cap with the air chamber, and (d) determining presence or absence of the controlled substance in the saliva sample based on presence or absence of a signal from the sensor cartridge.

In some embodiments, the controlled substance is a cannabinoid, an opioid, a stimulant, or a central nervous system (CNS) depressant. In some embodiments, the cannabinoid is tetrahydrocannabinol (THC) or tetrahydrocannabivarin (THCV). In some embodiments, the opioid is selected from the group consisting of codeine, fentanyl, heroin, hydrocodone, hydromorphone, morphine, and oxycodone. In some embodiments, the stimulant is an amphetamine or cocaine. In some embodiments, the amphetamine is selected from the group consisting of 3,4-methylenedioxy-methamphetamine (MDMA), dextroamphetamine, methamphetamine, and methylphenidate. In some embodiments, the CNS depressant is a barbiturate or a benzodiazepine.

In some embodiments, the oral swab is rolled in the mouth of the subject.

In some embodiments, steps (a)-(f) are performed in a total of 1 to 10 minutes.

In some embodiments, methods described herein further comprise loading the sensor cartridge into the detection cradle, and determining amount of the controlled substance in the saliva sample based on amount of signal detected from the sensor by a detection device positioned in the detection cradle.

In some embodiments, the detection device is a mobile electronic device. In some embodiments, the mobile electronic device is a mobile phone or a portable computer.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

Various aspects and embodiments will be described with reference to the following figures. The figures are not necessarily drawn to scale.

FIG. 1A is an image of the EPOCH system. The system had three modules: i) a processing kit for saliva extraction and labeling with AuNPs; ii) an injection-molded cartridge housing membrane sensors; and a docking-cradle containing optical parts for signal detection. The processing kit, mating with the sensor cartridge, delivered AuNP-saliva mixture to test and control sites. The sample-spotted cartridge was inserted to the cradle and imaged by a smartphone camera.

Figure 1B:
FIG. 1B is an image of a prototype of the EPOCH system. The sensor cartridge was fabricated in plastics for mass production. A custom-developed app automatically recognized and analyzed the sensing spot.

The details of one or more embodiments of the invention are set forth in the description below. Other features or advantages of the present invention will be apparent from the following drawings and detailed description of several embodiments and also from the appended claims.

DETAILED DESCRIPTION

The present disclosure is based, at least in part, on the development of methods and devices for detecting a controlled substance in a sample from a subject. As used herein, a "controlled substance" refers to any consumable drug, chemical, or substance that is controlled by government regulations. Controlled substances can be prescription-controlled substances, illegal controlled substances, or legal controlled substances.

*Cannabis* is currently approved for medicinal purposes in 34 US states and for recreational use in 15[27]. Given the legal consumerization of THC products and shops selling a variety of products, the number of users is on the rise. Easy accessibility to THC also raises concerns for misuses (e.g., overdose, consumption by minors) and accidents under drug's influence. In parallel, the potency of THC plant products has increased raising concerns about safety levels in individuals and to the public.

Consequently, it would be desirable to have rapid quantitative tests to measure and monitor THC concentrations in individuals. The systems described herein mitigate such THC-associated risks. The systems, including the exemplary EPOCH system, can have one or all of the following advantages: i) the assay is fast (3 min. sample-in-result-out) and robust to common interfering factors found in oral fluid; ii) it produces quantitative data comparable to GC-MS; iii) the detection limit (0.17 ng/mL) is below the regulatory guideline (1 ng/mL); and iv) the injection-molded cartridge and compact detection system enable on-site testing. In a proof-of-concept study using oral fluid samples from *cannabis* smokers and non-smokers, the exemplary EPOCH tests achieved excellent accuracy.

Several currently available analytical tests can detect THC in human bodily fluids. The gold standard, gas chromatography-mass spectrometry (GC-MS) of blood and urine samples, is generally performed in specialized laboratories and can take days to process[14, 15]. Test results can also be ambiguous in determining the last time of *cannabis* consumption[16, 17]. Residual THC and its metabolites are often present in bodies weeks after *cannabis* intake, and it is challenging to separate acute recent use from chronic use[17-20]. Conversely, high THC levels in oral fluid have been shown to directly correlate with immediate (<12 hrs) *cannabis* use[21-23]. Monitoring oral THC levels can thus enable a range of safety applications: precautionary self-monitoring by *cannabis* users, roadside testing by law enforcement, and drug screening in the public sector. Unfortunately, existing commercial test kits have suboptimal analytical capacities (e.g., low sensitivity, binary results) and laboratory-based tests require sophisticated instrumentation, a drawback to routine, on-site THC detection[24-26]. Details for existing commercials test kits are provided below:

plify sample handling and to maintain the optimal stoichiometry between saliva and reagents (e.g., saliva:AuNPs, 20 μL:50 μL) that yields consistent, quantitative, and inter-comparable results. This capacity promoted assay reproducibility and enabled THC quantification and comparison among different samples. Third, transmission optics for signal detection, exploiting the enhanced light penetration in a wet membrane, was adopted. Both theoretical calculations and experimental data confirmed that the transmission mode generated larger signal changes than the conventional reflective detection. Combined, these technical advances effectively transformed qualitative lateral flow assays into fast, quantitative analytical tests whose accuracy was comparable to that of laboratory-based tests (e.g., GC-MS).

Saliva is an appealing alternative to urine as a drug-testing matrix. From the logistic aspect, saliva can be collected almost at any location and under observation, minimizing the chance of alteration. More importantly, THC levels in saliva were shown to reflect those in blood after *cannabis* smoking or vaping[28], but were not influenced by oral intake of therapeutic capsules (e.g., dronabinol)[29]. As such, high THC levels in saliva can be an effective indicator of recent *cannabis* uses and potential drug-induced impairment[30,31]. Measuring THC in saliva is also less prone to concentration-

| | Name | Methods | Sample | Assay time (min) | Sensitivity (ng/mL) | Price per test | Detection | Quantitative assay | Link |
|---|---|---|---|---|---|---|---|---|---|
| Commercial tests | SalivaConfirm ™ Saliva Drug Test | LFA | Saliva | 10 | 25 | 6 | Naked eyes | N | 1 |
| | NarcoCheck THC Saliva Test | LFA | Saliva | 10 | 25 | 9.9 | Naked eyes | N | 2 |
| | UTest-O-Meter | LFA | Urine | 5 | 15 | 7 | Naked eyes | Y* | 3 |
| | EZ Key Cup 3 | LFA | Urine | 5 | 50 | 4.5 | Naked eyes | N | 4 |
| | NarcoCheck THC urine test | LFA | Urine | 5 | 50 | 3.9 | Naked eyes | N | 5 |
| | DrugConfirm ™ CLIA Urine Test | LFA | Urine | 10 | 50 | 2 | Naked eyes | N | 6 |
| Under development | Hound Labs marijuana breathalyzer | Rhodamine 123 based fluorescence | Breath | <5 | 1 pg/L (air) | N/A | Specific reader | N/A | 7 |
| | Cannabix technologies THCBA | | Breath | 5 | N/A | N/A | Specific reader | N/A | 8 |

*Discrete multi-level detection of 15, 50, 100, 200, and 300 ng/mL;
LFA, Lateral Flow Assay;
1. confirmbiosciences.com/shop/5-panel-salivaconfirm-premium-saliva-drug-test/
2. narcocheck.com/en/saliva-drug-tests/thc-marijuana-saliva-test.html
3. utestdrugtesting.com/product/utest-o-meter/
4. ezkeycup.com/product/ez-key-cup-3/
5. narcocheck.com/en/urine-drug-tests/thc-test-marijuana.html?search_query=urine+thc&results=42
6. confirmbiosciences.com/shop/5-panel-drugconfirm-clia-urine-drug-test-dip-card/
7. houndlabs.com/
8. cannabixtechnologies.com/

The exemplary EPOCH test described herein achieved an excellent accuracy when compared to existing tests including GC-MS. Several engineering features resulted in the excellent analytical capability of the methods described herein, e.g., EPOCH. First, a new cartridge design, a disk-shaped MCE membrane with a small orifice inlet can be included. This geometry supported higher flow rate (i.e., faster assay) than a conventional strip design, at the same time concentrating input samples to a small sensing area for higher sensitivity. Further, an analytical model for the fluidic behavior was developed and design parameters (e.g., disk radius, inlet size, membrane types) were engineered for assay speed (<3 min) and sensitivity (<1 ng/mL). Second, the preprocessing kit described herein can be used to sim-dependent effects occurring in urine. While saliva is ideal, the present analysis methods and systems can also be applied to other body fluids including breast milk[32]. Another application of the present methods is in testing *cannabis* products for their THC contents, to safeguard users from accidentally consuming highly concentrated THC products.

In some embodiments, separate modules can be integrated into a single automated device to enhance assay throughput and reliability. Also, the present devices can be augmented by incorporating on-screen cognitive function tests, such as the digit symbol substitution test (DSST)[33,34], which can be administered while the saliva assay is in progress. As in the case of alcohol testing, combining molecular and cognitive tests would enable a more accurate assessment of drug-induced impairment. Signal amplification can be used to further boost the assay sensitivity. For example, for qualitative tests, silver enhancement can be used to deposit metallic silver over AuNPs; this process will lower the detection limit (about 10-fold) by intensifying optical density at the detection spots[35]. Using novel nanomaterials (e.g., Au nanocages[36] or multimeric Au complexes[37]) would be an alternative way to intensify optical signal while maintaining analytical resolution. These strategies can be used to render the present assays comparable to ELISA in sensitivity but much faster in assay turnaround (<5 minutes vs. 1-3 hours). The testing targets can be expanded to include a broader panel of drugs. Besides THC, other psychoactive substances, including opiates, amphetamines, cocaine and benzodiazepines, have been shown to be present in saliva after their recent use. It is thus conceivable to run on-spot, multi-panel EPOCH tests from a single saliva specimen to rapidly identify drug types and initiate treatment for overdoses (e.g., naloxone for opiates). Thus, the present methods and devices provide a cost-effective, versatile analytical platform with applications in the roadside as well as in workplaces and laboratories.

Accordingly, provided herein are methods and devices that involve competitive immunoassays for detection of controlled substances (e.g., THC, opiates, amphetamines, cocaine, benzodiazepines).

I. Competitive Immunoassay Reagents

Methods described herein involve a competitive immunoassay that uses assay reagents including a detection probe, a capture probe, and a loading control probe.

Detection Probe

The methods and devices described herein involve detection of a controlled substance using a detection probe that binds to the controlled substance. The detection probe for use in these methods and devices disclosed herein can be any molecule (e.g., a protein, a polypeptide, or a small molecule) capable of binding to the controlled substance. For example, when the present methods and devices are used to detect THC, the detection probe can comprise an antibody that binds THC. Antibodies that bind to THC are commercially available, e.g., from Abcam; Abnova Corporation; Absolute Antibody; American Research Products Inc.; antibodies-online; Bethyl Laboratories, Inc.; Bio-Rad; Biorbyt; Bioss Inc.; BosterBio; Cell Signaling Technology; Creative Biolabs; Creative Diagnostics; EastCoast Bio; Fitzgerald Industries International; GeneTex; LifeSpan BioSciences; MyBioSource.com; Novus Biologicals; OriGene Technologies; ProSci, Inc; Proteintech Group Inc; R&D Systems; RayBiotech; Santa Cruz Biotechnology, Inc.; St John's Laboratory; Thermo Fisher Scientific; and United States Biological, or can be generated using methods known in the art. Antibodies or other molecules that bind to tetrahydrocannabivarin (THCV)), opioids (e.g., codeine, fentanyl, heroin, hydrocodone, hydromorphone, morphine, oxycodone), stimulants (e.g., 3,4-methylenedioxy-methamphetamine (MDMA), dextroamphetamine, methamphetamine, methylphenidate), and/or central nervous system (CNS) depressants (e.g., barbiturates, benzodiazepines) can also be used.

In some examples, the detection probe releases a detectable signal. Alternatively, or in addition to, the detection probe is conjugated to a detectable label. As used herein, a "detectable label" refers to any molecule that is capable of releasing a detectable signal, either directly or in directly. For example, the detectable label is a metallic particle (e.g., gold (Au) particle, platinum (Pt) particle), a semiconductor particle (e.g., a quantum dot), a chromophore (e.g., anthracene), a fluorophore (e.g., fluorescein), or a combination thereof.

Capture Probe

The present methods and devices described herein involve detection of a controlled substance using a competitive immunoassay scheme that includes an unlabeled competitor (also referred to as a capture probe) of the controlled substance to be detected. The capture probe for use in the methods and devices disclosed herein can be any molecule that binds to the same site on the detection probe as the controlled substance. For example, when THC is the controlled substance, the capture probe comprises unlabeled THC.

In some examples, the capture probe can include one or more additional molecules. For example, when THC is the controlled substance, the capture probe comprises unlabeled THC conjugated with bovine serum albumin ($THC_{BSA}$) and an anti-BSA antibody ($Ab_{BSA}$) that captures the $THC_{BSA}$. In another example, when THC is the controlled substance, the capture probe comprises $THC_{BSA}$, $Ab_{BSA}$, and IgG antibody ($Ab_{IgG}$) that captures $Ab_{BSA}$-$THC_{BSA}$ complexes.

Loading Control Probe

The present methods and devices described herein involve validation of sample loading using a loading control probe that binds to the detection probe. The loading control probe for use in the methods and devices disclosed herein can be any molecule (e.g., a protein, a polypeptide, or a small molecule) capable of binding to the detection probe. For example, when the detection probe comprises THC antibody-coated gold nanoparticles (AuNPs), the loading control probe can comprise IgG antibody ($Ab_{IgG}$) that captures the THC-AuNP complexes.

II. Devices

Aspects of the present disclosure provide a device for detecting a controlled substance in a sample comprising such. Reference is now made to the Figures, which illustrate pictorially various embodiments of a device described herein.

Figure 18:
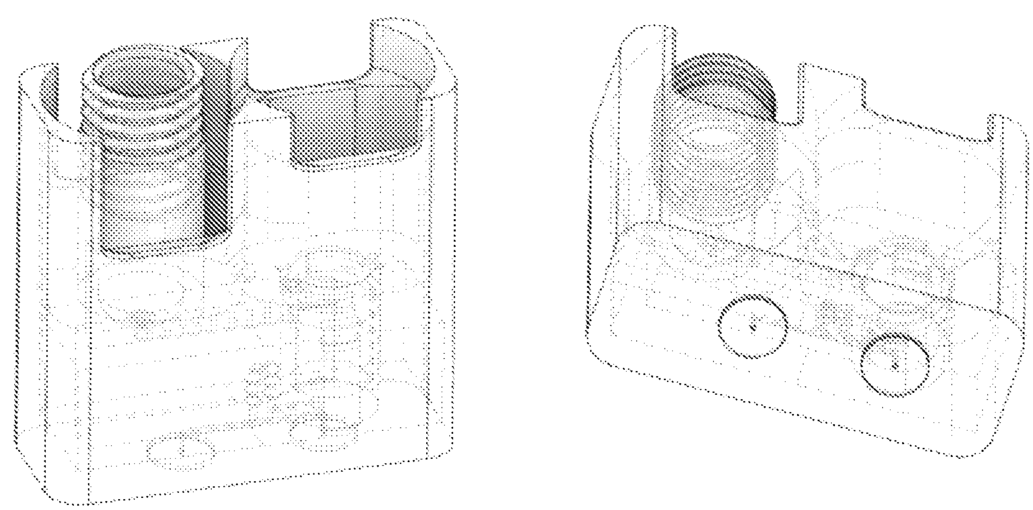
FIG. 18 is an image of a sample processing module, in accordance with some embodiments of the technology described herein.
Figure 19:
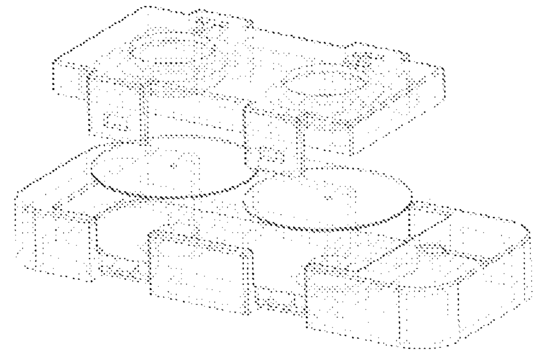
FIG. 19 is an image of a sensor cartridge, in accordance with some embodiments of the technology described herein.
Figure 19:
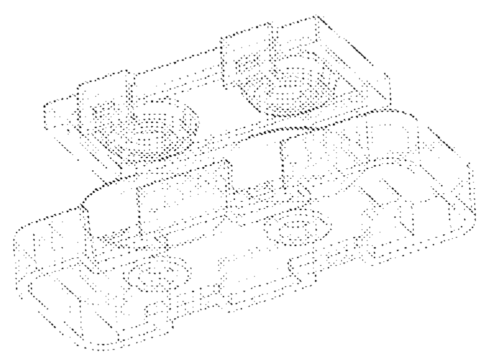
Figure 20:
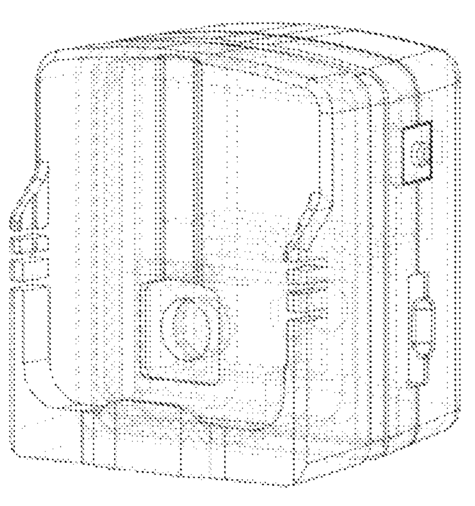
FIG. 20 is an image of a detection cradle, in accordance with some embodiments of the technology described herein.
Figure 20:
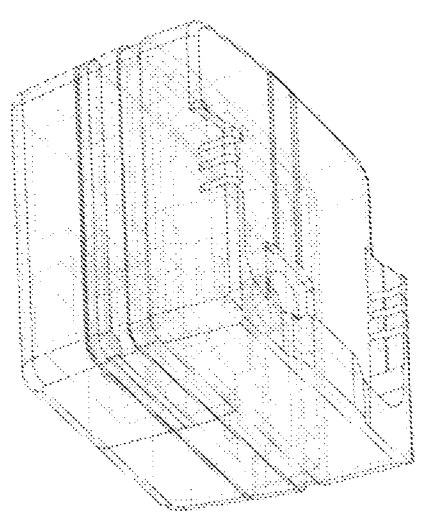

As show in FIG. 1A, the device, in some embodiments, comprises a sample processing module, a sensor cartridge, and a detection cradle. Layered drawings of the processing module, the sensor cartridge, and the detection cradle are shown in FIGS. 18-20, respectively.

The device described herein can be manufactured from any material rigid enough to allow the device to be manipulated by hand. Suitable materials include, for example, polymeric materials such as polycarbonate, polymethyl methacrylate, polypropylene, styrene acrylonitrile, polyvinyl chloride, polyvinylidene chloride, polyethylene tetraphthalate, or combinations thereof. In some examples, the device comprises one or more additives that aid fluid flow or that render the material biocompatible.

Figure 2A:
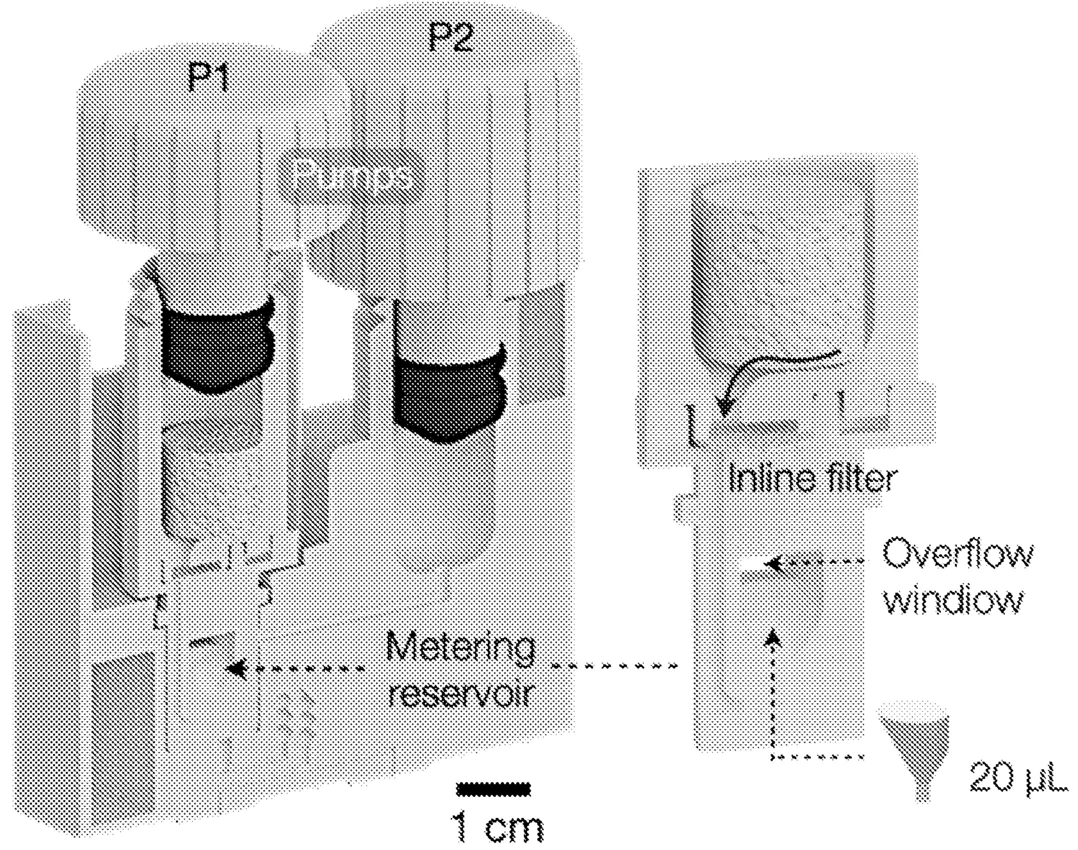
FIG. 2A is an image of the EPOCH processing kit. A disposable processing kit was designed to extract saliva and mix it with AuNPs. The kit had two screw-type actuators (P1, P2) for pumping. The metering reservoir (inset) had an inline filter (pore diameter: 0.45 μm cut off) and collected a fixed volume (20 μL) of saliva.
Figure 2B:
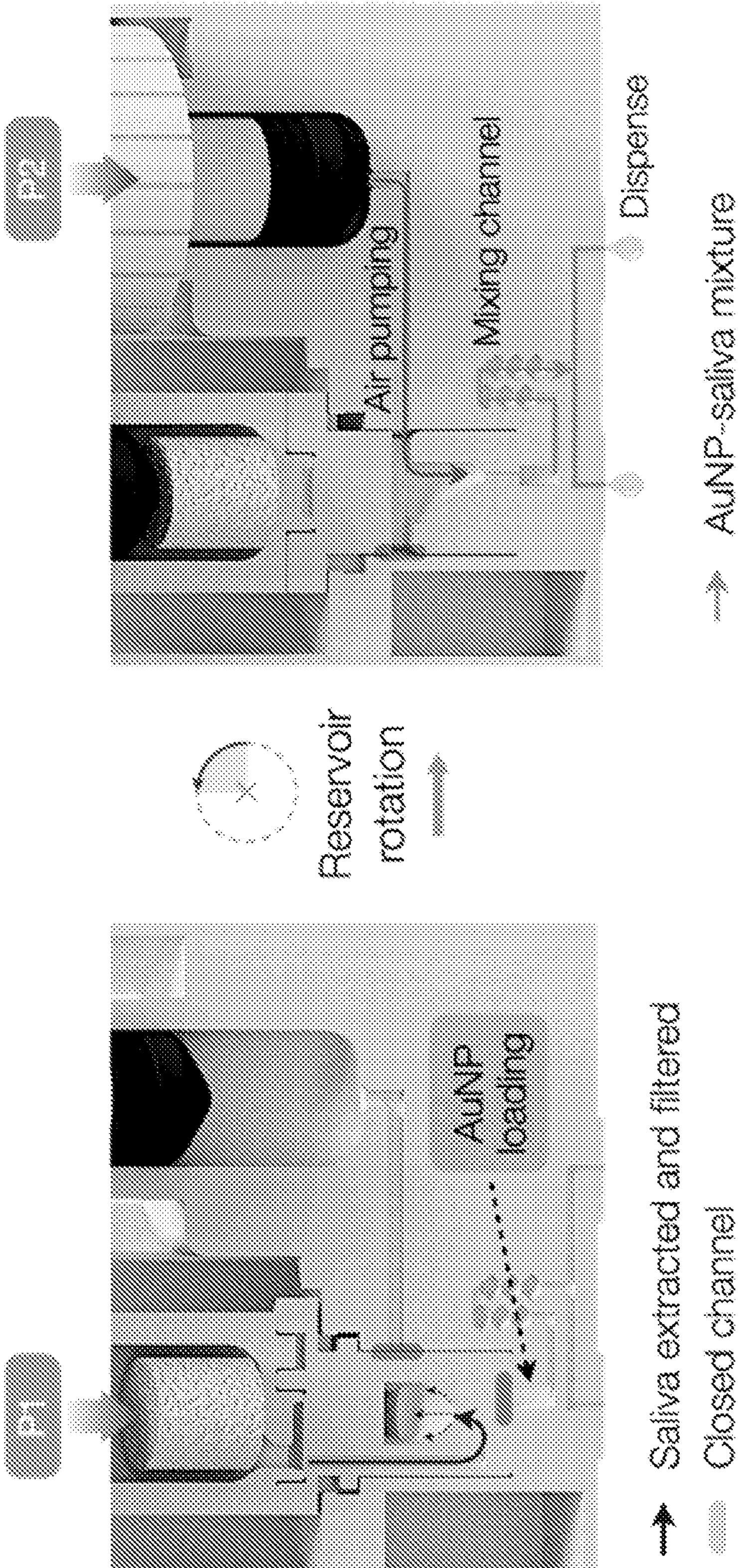
FIG. 2B is a schematic depiction of two-step sample processing. [Step 1] User advances P1 through twisting motion, which squeezes the collection swab and collects saliva in the reservoir. Excess saliva exits through the overflow window; paths to other fluidic channels are initially blocked. At the end of P1 twisting, the reservoir rotates 90° and makes a connection to the AuNP chamber. [Step 2] Twisting P2 transports saliva to AuNPs and pushes the mixture through the stirring channel. The final sample is then divided and delivered to the detection cartridge. The operation time is 1 min.

As shown in FIGS. 2A-2B, the sample processing module, in some embodiments, comprises an air chamber, a sample chamber, a metering reservoir, and a loading chamber.

The metering reservoir is reversibly connected to the sample chamber, the air chamber, and the loading chamber via the first, second, and third fluidic channels, respectively. The metering reservoir measures the amount of sample, which is then moved to the loading chamber that is preloaded with a detection probe. Excess sample overflows from the metering reservoir to the waste chamber via a syphon.

The metering reservoir is positionable to control flow of the sample. For example, when the sample is loaded into the sample chamber, the metering reservoir is positioned such that the sample can move from the sample chamber to the metering reservoir via the fluidic channel and excess sample can move from the metering reservoir to the waste chamber via the syphon. When the metering reservoir is in this position, the fluidic channel between the metering reservoir and the sample chamber is open, the syphon is open, the fluidic channel between the metering reservoir and the air chamber is closed, and the fluidic channel between the metering reservoir and loading chamber is closed.

After the sample is collected in the metering reservoir, the metering reservoir is rotated to position the metering reservoir such that the sample can move from the metering reservoir to the loading chamber. When the metering reservoir is in this position, the fluidic channel between the metering reservoir and the sample chamber is closed, the syphon is closed, the fluidic channel between the metering reservoir and the air chamber is open, and the fluidic channel between the metering reservoir and the loading chamber is open. As such, the sample can no longer move from the sample chamber to the metering reservoir or from the metering reservoir to the waste chamber.

In some examples, the fluidic channel connecting the sample chamber and the metering reservoir comprises a filter to remove debris from the sample prior to entering the metering reservoir. Any filter suitable for removing debris from a sample can be used in devices described herein.

The sample volume collected in the metering reservoir can be varied to achieve detection of the controlled substance. In some examples, the metering reservoir has a sample volume of 5 to 50 μL. For example, the metering reservoir has a sample volume of 10 to 50 μL, 15 to 50 μL, 20 to 50 μL, 25 to 50 μL, 30 to 50 μL, 35 to 50 μL, 40 to 50 μL, 45 to 50 μL, 5 to 45 μL, 5 to 40 μL, 5 to 35 μL, 5 to 30 μL, 5 to 25 μL, 5 to 20 μL, 5 to 15 μL, or 5 to 10 μL.

The volume of the detection probe preloaded into the loading chamber can be varied to achieve detection of the controlled substance. In some examples, the volume of the detection probe preloaded into the loading chamber is 5 to 250 μL. For example, the volume of the detection probe preloaded into the loading chamber is 50 to 250 μL, 100 to 250 μL, 150 to 250 μL, 200 to 250 μL, 5 to 200 μL, 5 to 150 μL, 5 to 100 μL, 5 to 50 μL, or 5 to 25 μL.

The ratio of the volume of the sample to the volume of the detection probe can be varied to achieve detection of the desired controlled substance. In some examples, the ratio of the volume of the sample to the volume of the detection probe is 1:1, 1:1.5, 1:2, 1:2.5, 1:3, 1:3.5, 1:4, 1:4.5, or 1:5.

The sample is moved from the metering reservoir to the loading chamber by pumping air from the air chamber through the metering reservoir and loading chamber. The sample mixes with the detection probe in the loading chamber and then moves through the microfluidic mixer to openings for dispensing the sample into the sensor cartridge. For example, as shown in FIG. 2B, the sample processing module can comprise two openings including a test sample outlet and a control sample outlet. In some examples, when detecting presence or absence of multiple controlled substances, the sample processing module can comprise multiple outlets (e.g., 3 outlets, 4 outlets, 5 outlets, 6 outlets, 7 outlets, 8 outlets or more). The size of the outlet can be varied as necessary to achieve detection of the controlled substance. In some examples, the outlet of the sample processing module has a diameter of 0.1 to 0.8 mm 0.35 mm). In some examples, the outlets of the sample processing module are mated to the inlets of the sensor cartridge for seamless sample delivery.

The sample processing module comprises one or more actuators that provide a motive force for moving the sample and reagents such as the detection probe through the sample processing module and to the sensor cartridge. For example, the sample processing module can comprise a cap having a protrusion that forms a piston relative to the sample chamber and a cap having a protrusion that forms a piston relative to the air chamber. When the cap is engaged with the chamber, a force sufficient to move the sample through the sample processing module is produced.

The cap can engage the sample processing module using any method suitable for producing a force sufficient to move the sample. For example, the sample processing module comprises circumferential screw threads for engaging a cap comprising circumferential receiving threads.

The size and shape of the sample processing module can be varied as necessary to achieve detection of the controlled substance. In some examples, the sample processing module has dimensions of 14×50×55 $mm^3$ to 34×70×75 $mm^3$, e.g., 24×60×65 $mm^3$.

Figure 3A:
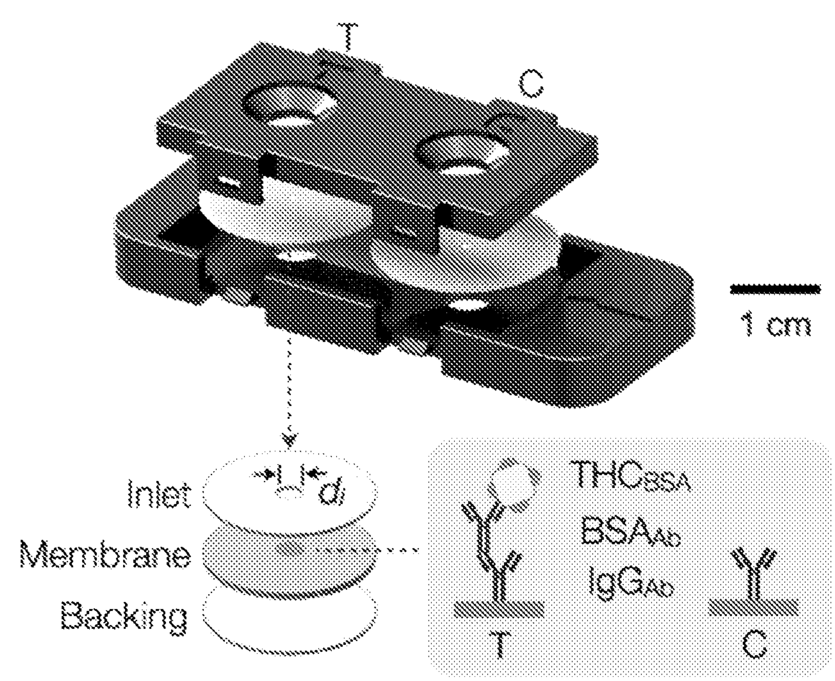
FIG. 3A is a schematic of an EPOCH cartridge. Two sensors, one for the loading control (C) and the other for THC quantification (T), were assembled into a disposable cartridge. Each sensor consisted of a radial membrane laminated with plastic films. Capture reagents were immobilized at the membrane center. The small inlet (diameter, $d_i$) confined AuNP and saliva mixture to pass through the capture region (circle identified by dotted line).

As shown in FIG. 3A, the sensor cartridge comprises a test membrane for detecting presence of the controlled substance in the sample and a control membrane that validates sample loading. The capture probe and the loading control probe are immobilized on the test membrane and the control membrane, respectively. In some examples, the test membrane and the control membrane are comprised in a housing that forms the sensor cartridge. In some examples, when detecting presence or absence of multiple controlled substances, the sensor cartridge can comprise multiple test and control membranes (e.g., 3 membranes, 4 membranes, 5 membranes, 6 membranes, 7 membranes, 8 membranes or more). In such instances, the sensor cartridge can comprise 1 test membrane and 1 control membrane for each controlled substance to be detected.

Any membrane suitable for immobilizing a capture probe or a loading control probe and detecting a signal generated therefrom can be used as a test membrane or a control membrane in methods and devices described herein. Non-limiting examples of a membrane (e.g., a test membrane or a control membrane) for use in the methods and devices described herein include a cellulose acetate (CA) membrane, a cellulose nitrate membrane, a glass-fiber membrane, a mixed cellulose ester (MCE) membrane, a polyvinylidene fluoride (PVDF) membrane, a polytetrafluoroethylene (PTFE) membrane, a polypropylene membrane, a polyethersulfone (PES) membrane, a polycarbonate track-etched (PCTE) membrane, and combinations thereof.

A membrane for use in devices described herein can have any shape and any size suitable for fluidic flow and detection of the controlled substance. In some examples, the control and test membrane are any shape and any size suitable for radial-membrane flow. For example, the control membrane and the test membrane are disk shaped. In such instances, the loading control probe and the capture probe are immobilized at the center of the control membrane and the test membrane, respectively. In some examples, when the control membrane and the test membrane are disk shaped, the membrane diameter is 10 to 30 mm (e.g., 20 mm).

The test membrane and the control membrane for use in devices described herein can have any pore size suitable for fluidic flow and detection of the controlled substance. In some examples, the pore size is 0.25 to 1.5 μm (e.g., 0.8 μm). For example, the pore size is 0.3 to 1.5 μm, 0.4 to 1.5 μm, 0.5 to 1.5 μm, 0.6 to 1.5 μm, 0.7 to 1.5 μm, 0.8 to 1.5 μm, 0.9 to 1.5 μm, 1.0 to 1.5 μm, 1.1 to 1.5 μm, 1.2 to 1.5 μm, 1.3 to 1.5 μm, 1.4 to 1.5 μm, 0.25 to 1.4 μm, 0.25 to 1.3 μm, 0.25 to 1.2 μm, 0.25 to 1.1 μm, 0.25 to 1.0 μm, 0.25 to 0.9 μm, 0.25 to 0.8 μm, 0.25 to 0.7 μm, 0.25 to 0.6 μm, 0.25 to 0.5 μm, 0.25 to 0.4 μm, or 0.25 to 0.3 μm.

The sample processing module and/or the sensor cartridge can comprise one or more components that provide structural support. For example, the control membrane and/or the test membrane can be sandwiched between plastic sealing films for structural support. In such instances, the sealing film includes an inlet hole at the center top of the film over each membrane that allows sample to enter the membrane from the outlet of the sample processing module. In some examples, the inlet hole has a diameter of 0.1 to 0.8 mm (e.g., 0.35 mm). In some examples, the diameter of the inlet hole of the sensor cartridge is the same or substantially the same as the diameter of the outlet of the sample processing module.

In some examples, the sensor cartridge can be detached from the sample processing module and attached to the detection cradle. In such instances, when attached to the sample processing module, the outlets of the sample processing module are mated to the inlets of the sensor cartridge for seamless sample delivery. When attached to the detection cradle, the sensor cartridge is aligned to the lens and the light source for optical signal detection.

Any detection device suitable for detecting an optical signal can be used in the devices described herein. In some examples, the detection device is a mobile electronic device such as a mobile phone or a portable computer. In such instances, methods described herein can comprise a computer implemented method for determining presence and/or amount of the controlled substance based on the optical signal from the sensor cartridge. Such methods can involve a software program (e.g., an app) for image acquisition and data analysis.

III. Detection of Controlled Substances

Also provided herein are methods for detecting a controlled substance in a sample from a subject using any of the devices described herein. Methods described herein can involve a competitive immunoassay that uses assay reagent including a detection probe, a capture probe, and a loading control probe, which are all disclosed herein.

In some embodiments, the methods can involve collecting a sample from a subject and contacting the sample with assay reagents (e.g., detection probe, capture probe, loading control probe) in a device as described herein for a time and under conditions sufficient for formation of a complex comprising the controlled substance and assay reagents, if any.

The sample is divided via channels in the sample processing module for loading onto the test membrane and the control membrane in the sensor cartridge of the devices as described herein. The test membrane can include an immobilized capture probe that captures detection probe free of the controlled substance. The control membrane can includes an immobilized loading control probe that captures a detection probe that is bound to and/or free of the controlled substance.

Presence or level of the controlled substance in the sample can be detected by measuring a signal released from the detection probe or a detectable label conjugated to the detection probe on the test membrane. Sample loading onto the control membrane can be validated by measuring a signal released from the detection probe or a detectable label conjugated to the detection probe on the control membrane.

Accordingly, methods described herein involve detection of a test signal that indicates presence/absence of the controlled substance in the sample and a control signal that validates sample loading. In some examples, the test signal and/or the control signal are detected by eye. Alternatively, or in addition to, the test signal and/or the control signal are detected using a detection device such as a mobile electronic device (e.g., a mobile phone, a portable computer). In such instances, the sensor cartridge is loaded into a detection cradle comprising optical components (e.g., lens, light-emitting diode (LED)) that convert light into an electrical signal for measurement and/or analysis using a detection device.

To perform methods disclosed herein, the sample can be processed and moved through the devices as described herein using an actuator, which can be a cap having a protrusion that forms a piston relative to a chamber (e.g., sample chamber) when the cap is joined to the chamber (e.g., sample chamber). An actuator can be used to move the sample from the sample chamber to the metering reservoir. In some examples, when the sample is collected using an oral swab, the actuator compresses the oral swab, thereby extracting saliva. An actuator can also be used to move the sample from the metering reservoir through the loading chamber and into the detection cartridge. Accordingly, methods described herein can involve engaging an actuator with the sample chamber and the air chamber.

Methods provided herein can encompass detecting a controlled substance, or lack thereof, in various samples from a subject. The methods can include detecting one or more controlled substances, e.g., 2 controlled substances, 3 controlled substances, 4 controlled substances, or more.

Any sample including or suspected of including a controlled substance can be used in methods described herein. In some examples, the sample is a saliva sample, a blood sample, a breath sample, a urine sample, a semen sample, or a breast milk sample.

Any method known in the art can be used to collect a sample from the subject. In some examples, when the sample is a saliva sample, the sample is collected using an oral swab that is rolled in the mouth of the subject, optionally rubbing the teeth and/or inside of the cheeks.

Sample collection methods can vary depending on the type of sample to be collected. For example, a saliva sample can be collected using an oral swab and a urine sample can be collected using a container.

Any controlled substance can be detected using methods and devices described herein. Non-limiting examples of controlled substances include cannabinoids (e.g., tetrahydrocannabinol (THC), tetrahydrocannabivarin (THCV)), opioids (e.g., codeine, fentanyl, heroin, hydrocodone, hydromorphone, morphine, oxycodone), stimulants (e.g., 3,4-methylenedioxy-methamphetamine (MDMA), dextroamphetamine, methamphetamine, methylphenidate), and central nervous system (CNS) depressants (e.g., barbiturates, benzodiazepines).

Methods for detecting a controlled substance described herein are rapid and can provide test results within minutes of sample collection. For example, methods described herein can provide test results in 1 to 10 minutes. In some examples, methods described herein can provide test results in no more than 10 minutes, no more than 9 minutes, no more than 8 minutes, no more than 7 minutes, no more than 6 minutes, no more than 5 minutes, no more than 4 minutes, no more than 3 minutes, no more than 2 minutes, or no more than 1 minute.

EXAMPLES

In order that the invention described can be more fully understood, the following examples are set forth. The examples described in this application are offered to illustrate the methods and compositions provided herein and are not to be construed in any way as limiting their scope.

Materials and Methods

The following materials and methods were used in the Examples set forth herein.

Sample Collection

This study was approved by the Institutional Review Board of Massachusetts General Hospital (IRB number 2019P003472, PI: Hakho Lee), and the overall procedures followed institutional guidelines suggested. Informed consent was obtained from all subjects (*cannabis* smoker n=27, non-smoker n=14). *Cannabis* users were asked to take saliva samples right after *cannabis* smoking. Specifically, they were instructed to take a disposable swab (diameter, 1 cm; length, 1.5 cm) into the mouth and roll it for about one minute. The swab was then placed into the sample processing kit. Control samples were collected in the same manner from volunteers who self-declared no history of *cannabis* use. For the time-course monitoring, three *cannabis* smokers collected saliva samples hourly after their last smoking. Cylindrical saliva swabs were purchased (SalivaBio Oral Swab, Salimetrics, USA). These swabs were cut in the middle of their height to fit into the sample processing kit. Each halved swab collected about 0.5 mL of saliva.

Preparation of Gold Nanoparticles Conjugated with THC Antibodies

Figure 16A:
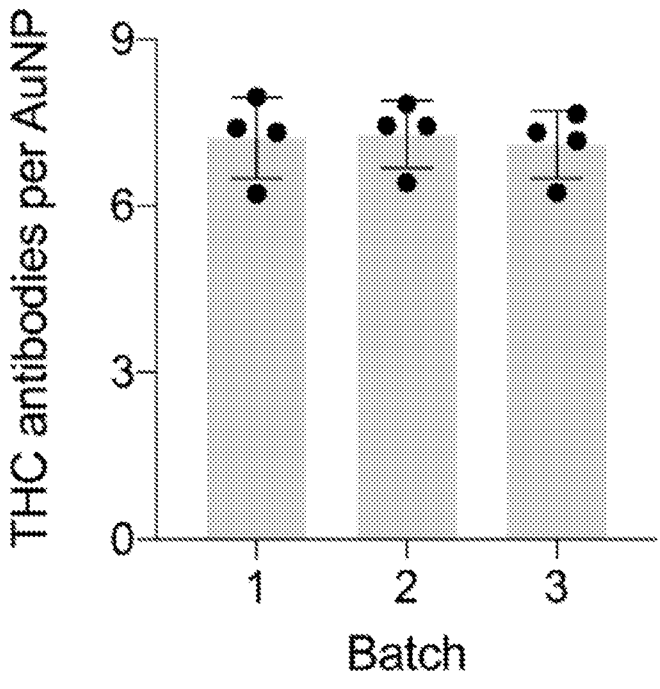
FIG. 16A is a graph of THC antibodies per AuNP. An o-phthalaldehyde (OPA) spectrophotometric assay was used to quantify THC antibodies on a 20 nm AuNP. OPA reacts with the amine group in antibodies, allowing for the quantitation of proteins and peptides. Fluoraldehyde OPA reagent solution (26025, Thermo Fisher Scientific, USA) was used for the assay. Three different batches were prepared, and each batch was measured in quadruplicate. The average number of THC antibodies per particle was 7.2.
Figure 16B:
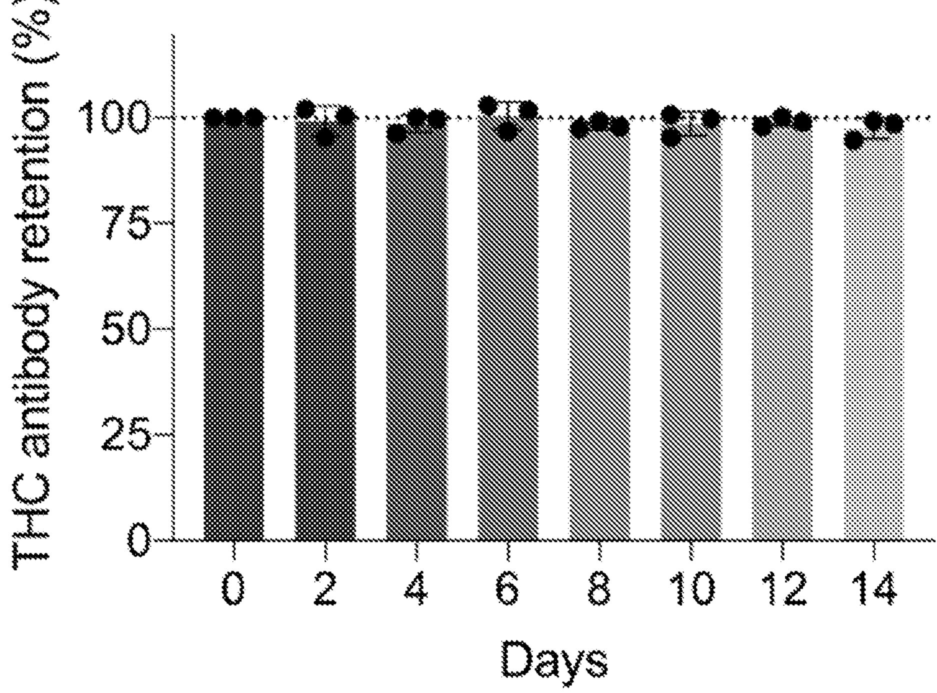
FIG. 16B is a graph of AuNP-antibody conjugate stability. Stability of AuNP-antibody conjugates was monitored. The particle-antibody conjugates were stored at ambient temperature (20° C.). AuNPs were collected via centrifugation (31000×g, 60 min), and the amount of antibodies in supernatant was quantified through the OPA assay. More than 95% of antibodies remained associated with AuNPs for at least 14 days. Three technical replicates were measured, and the data are displayed as mean±SD.

10 μL of 1 mg/mL THC antibody (Fitzgerald, USA) was added to a mixture of 1 mL of 20 nm colloidal gold nanoparticles (AuNPs; BBI solutions, UK) and 100 μL of 0.1 M borate buffer (Thermo Fisher Scientific, USA). After incubation at room temperature for an hour, 10 μL of 10% protein saver (Toyobo, Japan) was added to the mixture to block unreacted AuNP surface. The mixture was incubated at room temperature for an hour again and then centrifuged (8000×g) at 10° C. for 15 min. The supernatant was discarded, and the pellets were re-suspended in 10 mM borate buffer. The centrifugation and resuspension were repeated two times more. The final AuNP-antibody conjugate solution was prepared with 1% polyvinylpyrrolidone (MilliporeSigma, USA), 0.5% surfactant 10G (Fitzgerald), and 1% dimethyl sulfoxide (MilliporeSigma) in PBS. About seven THC antibodies were adsorbed on a single AuNP (FIG. 16A), and the conjugated particles were stable at least 2 weeks at ambient storage condition (FIG. 16B).

Sample Processing Kit

Figure 8A:
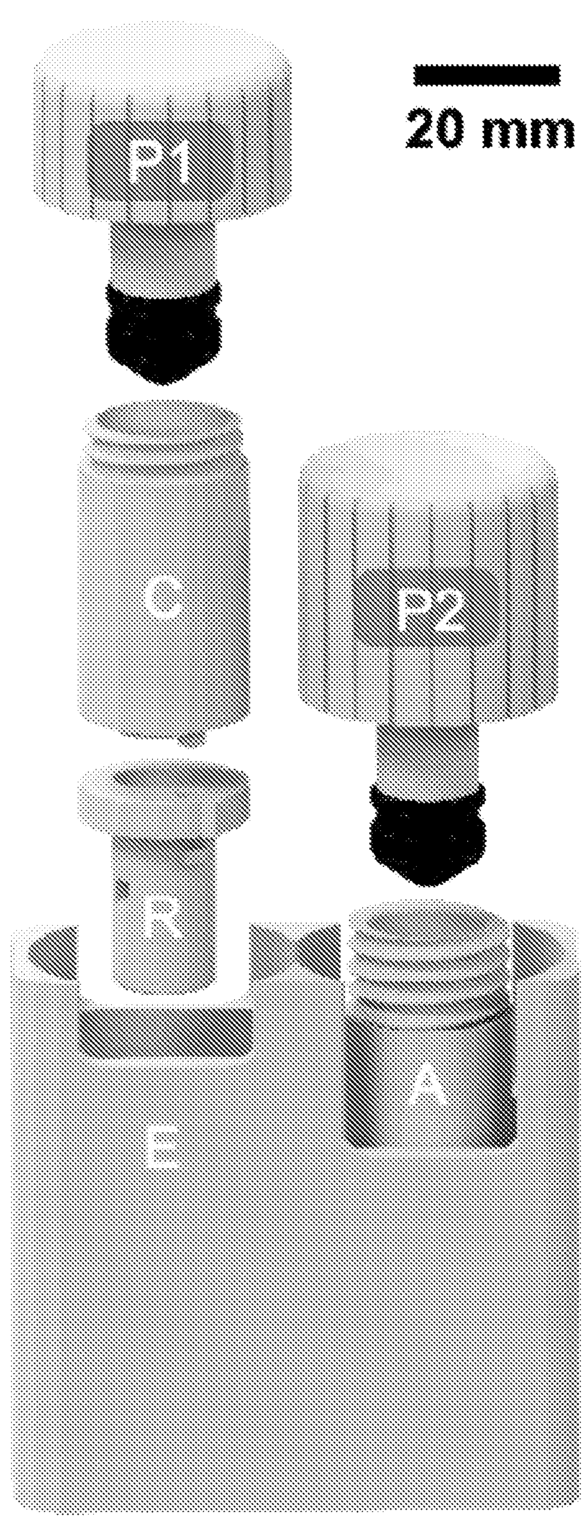
FIG. 8A is an exploded view of the processing kit. The extraction chamber (E) accommodates a twisting actuator (P1), a container for a saliva swab (C) and a metering reservoir (R). The air pump (A) is actuated by a twisting plunger (P2).
Figure 8B:
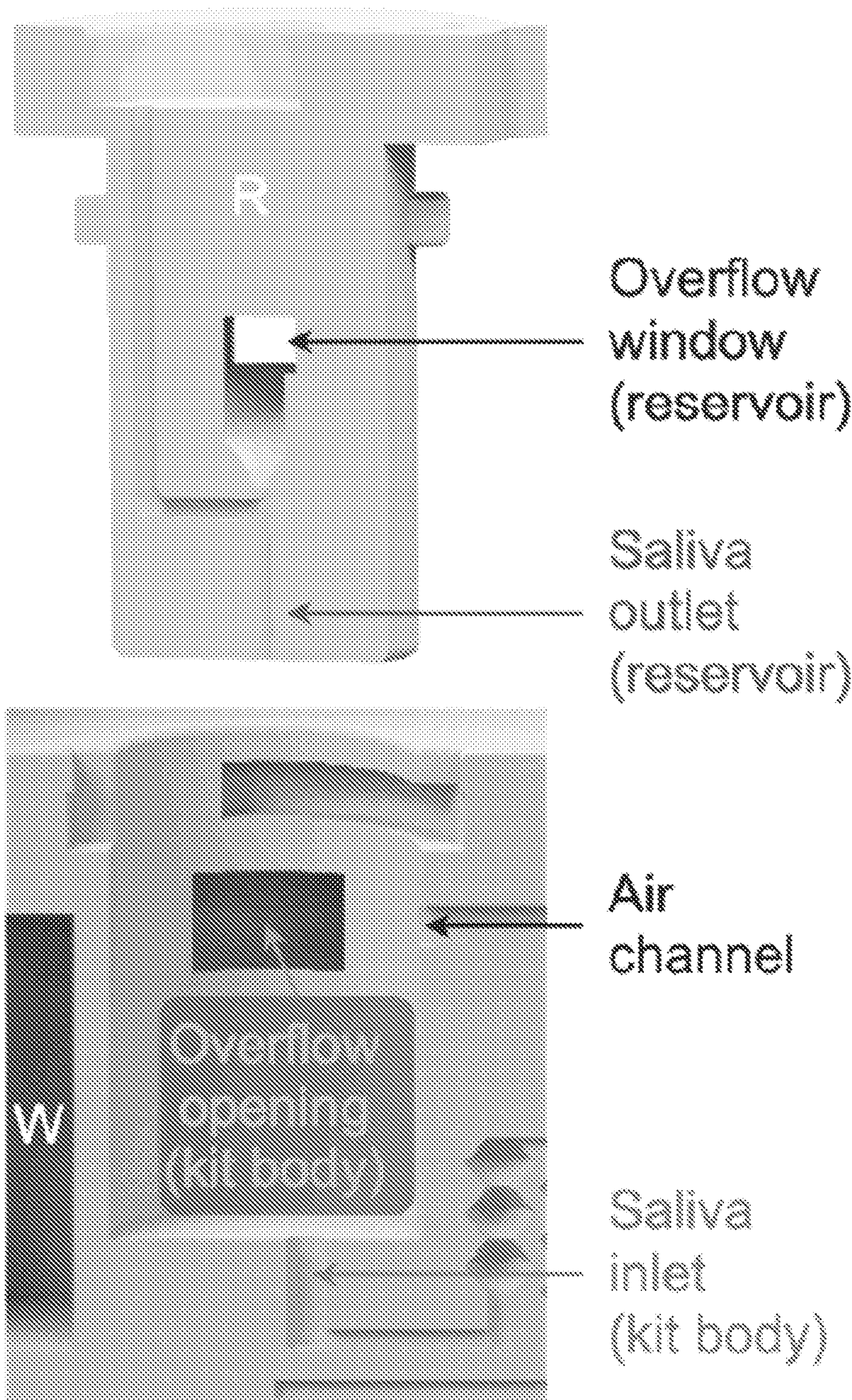
FIG. 8B is an exploded cross-section view of the processing kit that controls for internal flow saliva metering. The overflow window in the metering reservoir is initially aligned with the opening in the kit body. Excess saliva is collected into the waste chamber (W).
Figure 8C:
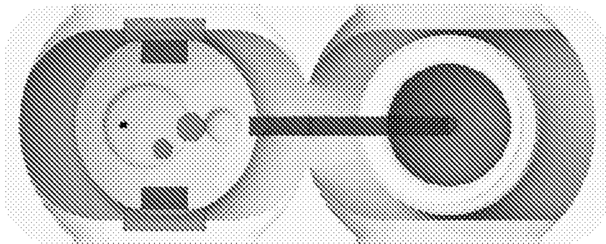
FIG. 8C are schematics of fluidic channel configurations. (i) During the saliva collection, overflow channels are open, but the saliva outlet in the metering reservoir is closed. Fixed amount of saliva (20 μL) is collected. (ii) At the end of saliva extraction, the metering reservoir rotates 90°, which connects the saliva outlet in the reservoir to the reagent channel in the kit body. Air channel is also connected to pump saliva through the reagent channel, the mixing chamber, and finally the dispense outlets.
Figure 8C:
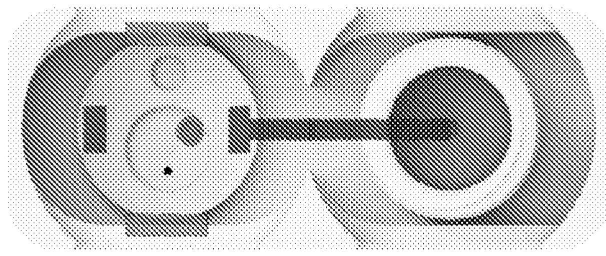

The device was designed to be injection-molded for mass production. For fast prototyping, mockup devices were fabricated via mechanical machining. Polycarbonate, which is one of the plastic materials for injection molding, was used as a structural material and machined via micromilling. The sample processing kit was divided into four parts: two halves inner for sample processing and two outer halves for sample storage. The assembled kit (24×60×65 mm$^3$) had two chambers, one for the saliva swab and the other for pumping. Each chamber was fitted with a plunger that could be manually actuated through twisting motions. Other key design features were the following. (i) In the swab chamber, an inline filter (pore size, 0.45 μm; HAWP02500, MilliporeSigma) was inserted to remove debris from native saliva. (ii) The saliva reservoir had an overflow opening to collect fixed volume of saliva (20 μL). The collected saliva was then mixed with AuNPs (50 μL) that were preloaded into the device. AuNPs were retained under the saliva reservoir with an off-axis flow alignment with the reservoir outlet (see FIGS. 8A-8C for details). (iii) The fluidic channel had a beehive-like structure to enhance the mixing between saliva and AuNPs. (iv) Two outlets of the processing kit mated to the inlets of the sensor cartridge for seamless sample delivery.

EPOCH Cartridge

The cartridge had two part, a bottom tray and a cover plate. These parts interlocked mechanically by snap-fit for easy assemble and uniform contact between membrane pads and plastic parts. Each cartridge contained two assay pads, one for a control and the other for THC test. The control assay pad was spotted with 1 μL of anti-mouse IgG (M8642, MilliporeSigma) to capture antibody-conjugated AuNPs. The signal from the control spot was visually inspected to validate the assay. The test pad was spotted with 1 μL mixture of THC-BSA hapten (80-1051, Fitzgerald), BSA antibody (ab3781, Abcam, UK), and anti-mouse IgG (See Table 1 for more detail), whose composition was experimentally optimized. Each individual pad was made of a 0.8 μm MCE membrane (diameter, 20 mm; AAWP02500, MilliporeSigma) sandwiched by two plastic films (SealPlate® film, MilliporeSigma). A 0.35-mm inlet hole was punched at the center of the top film before lamination. A pair of sensor pads (THC test and control) were placed on an additional film (41×20 mm$^2$; SealPlate®) to fix their relative spacing. The assembly was installed in the cartridge, keeping the pad inlets aligned with the cartridge openings. The cartridge was then put in a convection oven at 37° C. for an hour for drying.

TABLE 1

Characterization of THC-BSA mixture

| | THC-BSA hapten | BSA antibody | Anti-Mouse IgG |
|---|---|---|---|
| Molecular weight (kDa) | 70.3 | 155 | 166 |
| Concentration (mg/mL) | 1 | 1 | 0.1 |
| Mixing ratio | 1 | 1 | 2 |

Optical Detection Device

Figure 6A:
FIG. 6A is a schematic of the optical cradle. A smartphone is docked into the cradle and the sensor cartridge is inserted through a side slot.
Figure 6B:
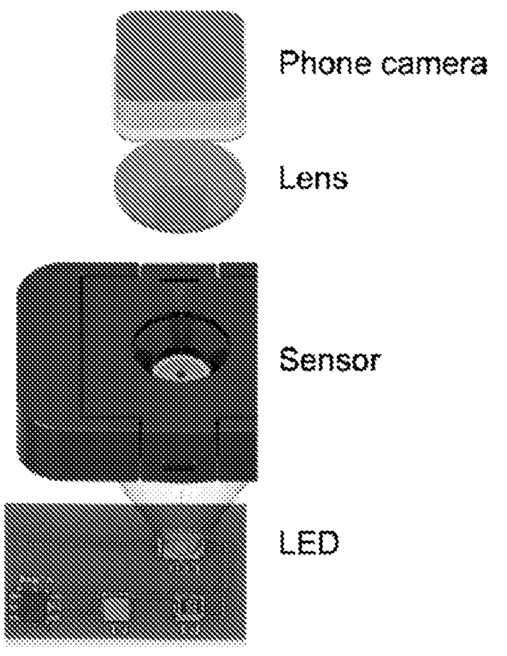
FIG. 6B is a schematic of the optical components and their alignment within the cradle. A 525-nm light emitting diode (LED) shines the membrane. The phone camera takes a close-up shot of the membrane in a transmission detection mode. A printed circuit board was custom-designed for LEDs and their current drivers. A 9V battery was used as a power source.
Figure 6C:
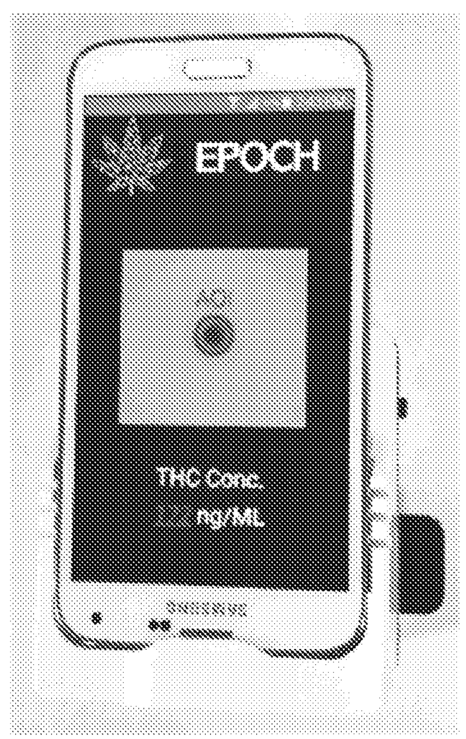
FIG. 6C is an image of the EPOCH cradle after whole device installation.

The cradle (80×85×65 mm$^3$) housed a printed circuit board for a 525-nm LED (XPEBGR, Cree Inc., USA), a convex lens (LB1844-A, Thorlabs, USA), a pushbutton switch for LED on-off control, and a 9V battery (FIGS. 6A-6C). The cradle was also designed to function as a base stand for signal measurements; it docked with a smartphone (Galaxy S5, Samsung, South Korea), had an insert for the sensor cartridge, and provided a lightproof dark environment. When the system was fully installed, the rear-facing phone camera, the lens, a detection spot in the sensor cartridge, and the LED were all aligned for the transmission image acquisition. Using the lens (focal length, 5 cm) allowed the camera to take a closeup of the detection spot at the same time shortening the working distance between the camera and the sensor cartridge (3.5 cm). The phone was inserted to the cradle upside-down, which deceased the overall cradle size.

Smartphone App

Figure 7A:
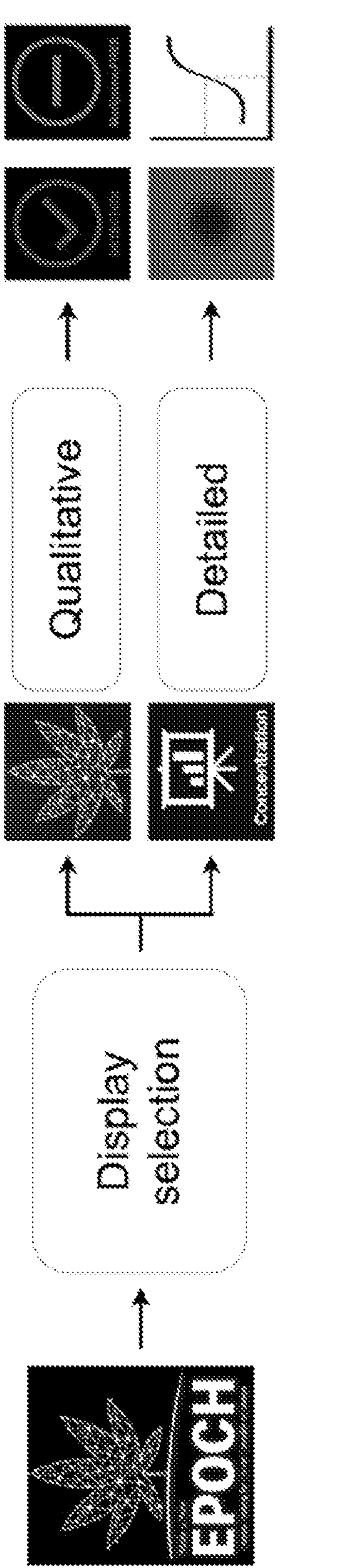
FIG. 7A is a schematic of a smartphone app developed to manage the operation of transmission-image capture, analysis, and display. Pushing the detection icon starts the measurement and displays qualitative results. The threshold for the positive detection is [THC]≥1 ng/mL. Users can tap the "Concentration" icon to access the measurement details (e.g., raw images, [THC] values).
Figure 7B:
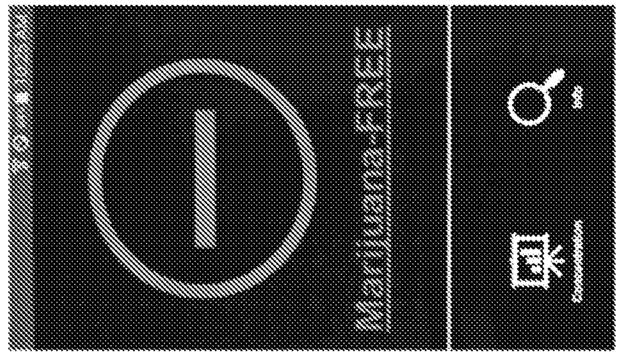
FIG. 7B are screenshots of the EPOCH app.
Figure 7B:
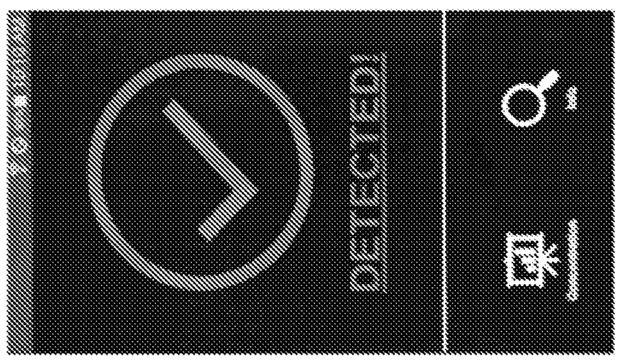
Figure 7B:
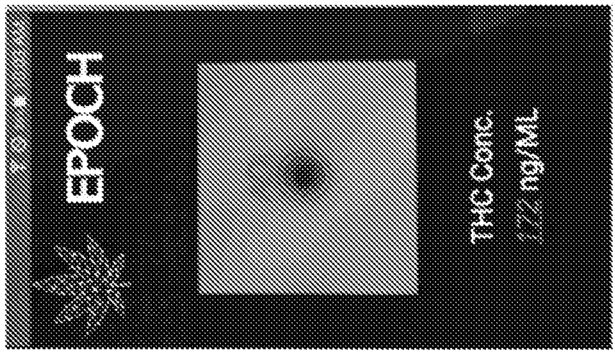
Figure 7B:
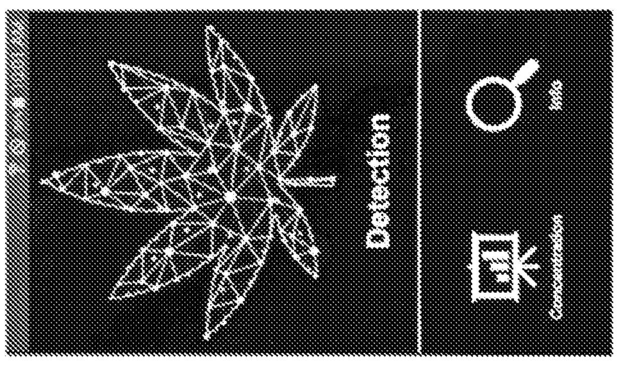

A smartphone app for image acquisition and data analyses was developed (FIGS. 7A-7B). For image analyses, the program automatically defined five regions of interest (ROIs) in a gray scale image: one $ROI_{AuNP}$ for the detection spot where AuNPs were bound, and the rest four $ROI_{REF}$ as a background reference (FIG. 13). The area of the $ROI_{AuNP}$ was the same as the area sum of four $ROI_{REF}$. For each ROI, the total pixel intensity was obtained, $I_{AuNP}$ from $ROI_{AuNP}$, and $I_{REF}$ from four $ROI_{REF}$. As an analytical metric, the EPOCH signal ($I_{EPOCH}$) was calculated as $I_{EPOCH}=(I_{REF}-I_{AuNP})/I_{REF}$. The app had an internal lookup table to convert IEPOCH to an estimated THC concentration in saliva. Each image with the ROI information was stored in a cloud server through phone's wireless connection. The app was written in JAVA using Android studio.

Gas Chromatography—Mass Spectrometry

Figure 17:
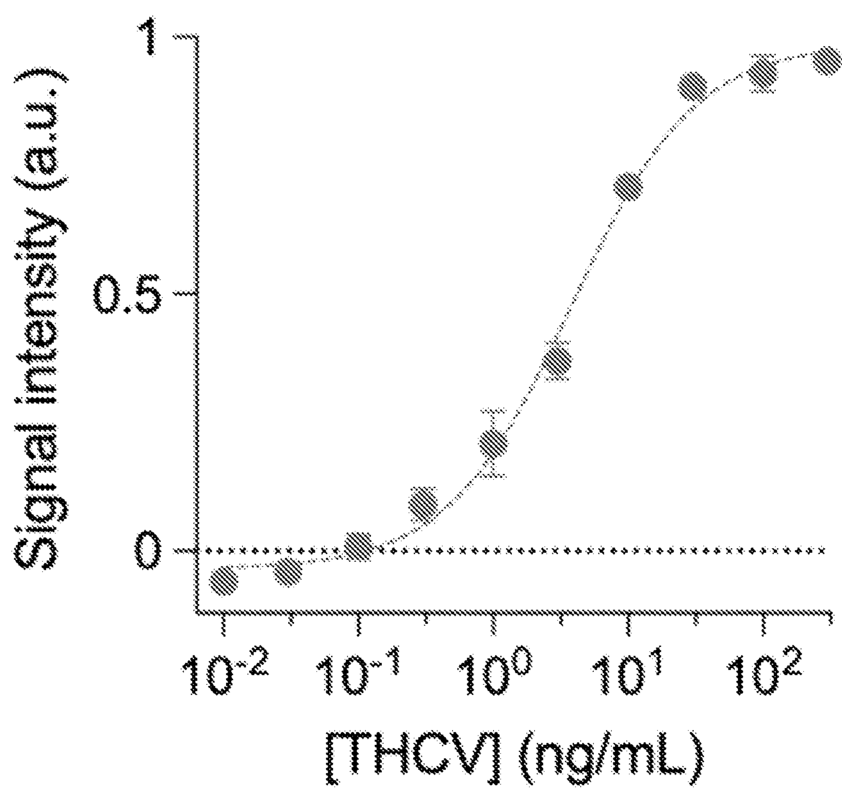
FIG. 17 is a graph of a titration curve for tetrahydrocannabivarin (THCV). The EPOCH sensor was used to detect THCV, an analogue of THC. The THCV titration curve was very similar to that of THC (see FIG. 4C), with the estimated limit of detection of [THCV]=0.2 ng/mL. These data were compared with GC-MS quantification. Data are displayed as mean±SD from technical triplicate measurements.

Due to a regulatory restriction, tetrahydrocannabivarin (THCV; T-094, Cerilliant, USA), an analog of THC, was used as a standard material for gas chromatography-mass spectrometry (GC-MS, 7890B-5977A, Agilent Technologies, USA). The initial THCV (1.0 mg/mL) was 2-fold serially diluted with methanol (MilliporeSigma) to 1.0 ng/mL. The dilute THCV samples were injected into GC-MS using an auto-sampler system (PAL, Agilent Technologies) with a 10 μL syringe at an injection volume of 2 μL. About 80% of the syringe volume was filled with methanol for the pre-cleaning process before measurement, followed by sample injection with the speed of 50 μL/s. The pre- and post-injection delay was 500 ms each. Initial GC temperature was set to 30° C., and the temperature gradually rose at a rate of 30° C./min until it reached 325° C. GC column (19091S-433, Agilent technologies) was utilized with 6.4845 psi pressure, 1 mL/min phase moving speed (average speed of 36.074 cm/sec), resulting in 1.386 min holding time. The acquisition mode was set to SIM/scan method. For comparison, an EPOCH sensor for THCV was also designed and a dose-dependent titration curve was obtained (FIG. 17).

Example 1: EPOCH Assay Design

Figure 1C:
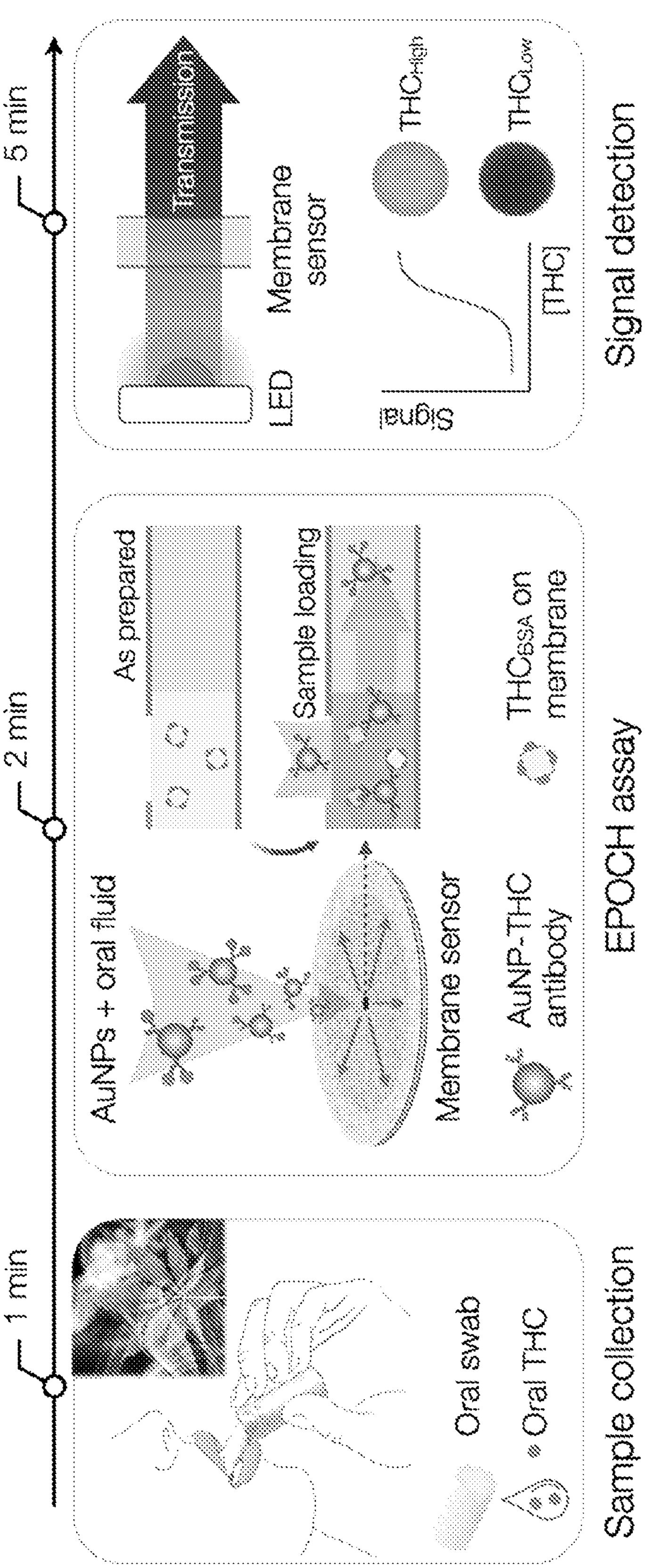
FIG. 1C is a schematic depiction of 5 minute THC detection using the EPOCH system. (Left) A test sample is collected using an oral swab. (Middle) oral fluid is extracted and mixed with THC-specific gold nanoparticles. The mixture is then spotted on a radial membrane sensor that has immobilized THC competitors (THC haptens conjugated to BSA carriers; $THC_{BSA}$). (Right) $AuNP_{Ab}$ differentially binds to $THC_{BSA}$ according to oral THC concentration. Transmission through the sensing spot is digitized for THC quantification.

FIG. 1C summarizes the EPOCH assay. Given the ease of collection, robust correlation and limited variability, the test was based on sputum rather that blood, breath or urine samples. The EPOCH test device (FIGS. 1A-1B) comprised a saliva processing module, a sensor cartridge, and an optical detection cradle. Saliva is sampled via a mouth swab. The swab is then processed into a custom-designed extraction kit that mixes saliva with preloaded THC antibody-coated gold nanoparticles (AuNPs). A competitive immunoassay scheme (FIG. 1C), which is ideally suited to detect small molecules such as THC, was used. The THC-AuNP complexes are then injected onto the membrane sensor wherein THC competitors (THC conjugated with bovine serum albumin; THC-BSA) is immobilized. The sensor cartridge is then inserted into the cradle for optical alignment with a light emitting diode (LED), a macro lens, and a smartphone camera. A sensing spot was imaged by taking a close-up shot of transmission signals from the membrane sensor. A smartphone App to provide user-interfaces for image acquisition, automated image analysis, and data storage in a cloud server was also developed (Methods for details; FIGS. 7A-7B). The entire assay completes within 5 min and requires <100 μL of saliva (a single swab).

Figure 2C:
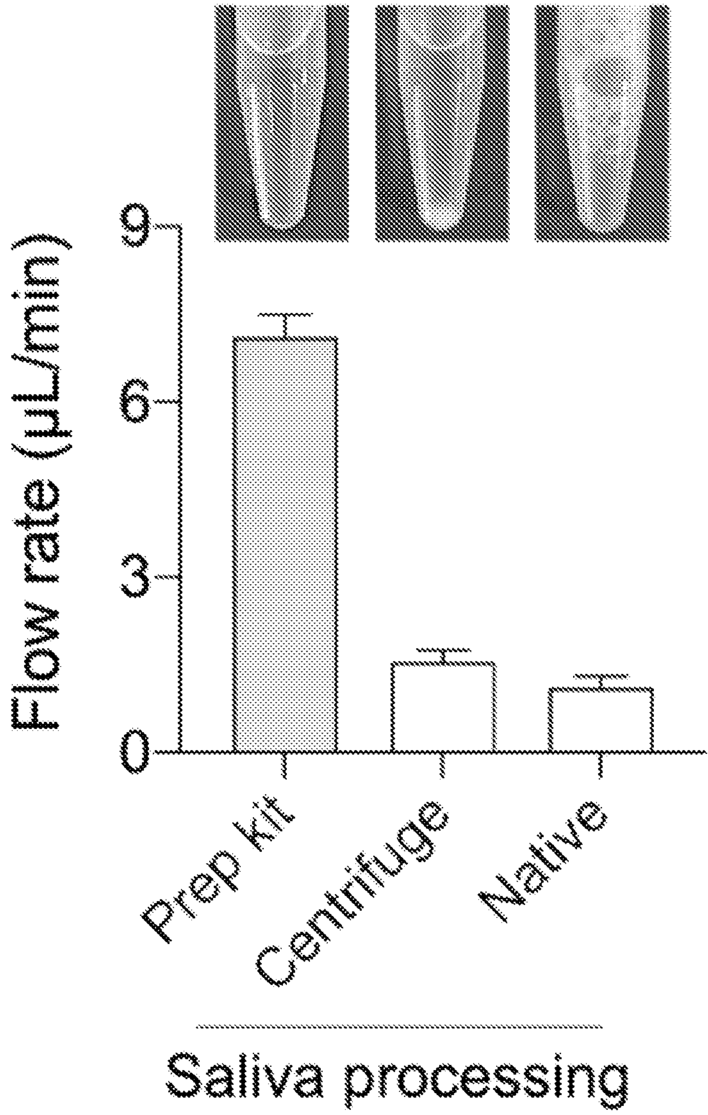
FIG. 2C is an image and graph showing that the processing kit ensured high, consistent saliva flow in the membrane sensor, clearing samples from debris. The bar represents mean±SD from technical triplicates.

The sample processing kit allowed to perform multiple assay steps in a single device: i) extracting saliva from an oral swab, ii) mixing saliva with AuNPs at the optimal ratio, and iii) injecting the mixture to the sensor cartridge. The inline filtration cleared debris in saliva (FIG. 2C) to promote sample flow through membrane sensors; the metering mechanism ensured consistent stoichiometry, rendering the assay quantitative and inter-comparable. The sample processing module performs multiple pre-analytical steps with a simple manual actuation (FIG. 2A and FIGS. 8A-8C). The first step actuates a plunger in an extraction cylinder (FIG. 2B, left). In a single twist motion, saliva was drawn out from a swab, passed through an inline filter (0.45 μm pore), and collected in a metering reservoir that had a fixed retention volume (20 μL). A second twist motion through the air chamber (FIG. 2B, right) then combined the collected saliva with preloaded AuNPs (50 μL), and pushed them through a mixing channel. Finally, the mixture was dispensed as two aliquots (~18 μL each), one for a control and the other for THC detection; the sensor cartridge mated with saliva processing module's outlets for seamless sample transfer. All disposable parts (i.e., the processing unit and the cartridge) were designed to be compatible with producing with plastic injection molding (Methods for details); their layouts were optimized to meet machine tooling factors.

Example 2: Membrane Sensor Construction

One of the design considerations was rapid assay speed while maintaining high sensitivity. The sensor consisted of a membrane sandwiched between plastic sealing films for a structural support (FIG. 3A). AuNP-saliva mixture was injected through a small inlet (diameter, di) located at the membrane center; this configuration confined the input sample to pass through the small sensing zone (FIG. 1B), intensifying the analytical signal. Two membrane pads were embedded in a single cartridge: a test pad to detect THC in saliva and a control pad to validate sample loading.

Figure 9:
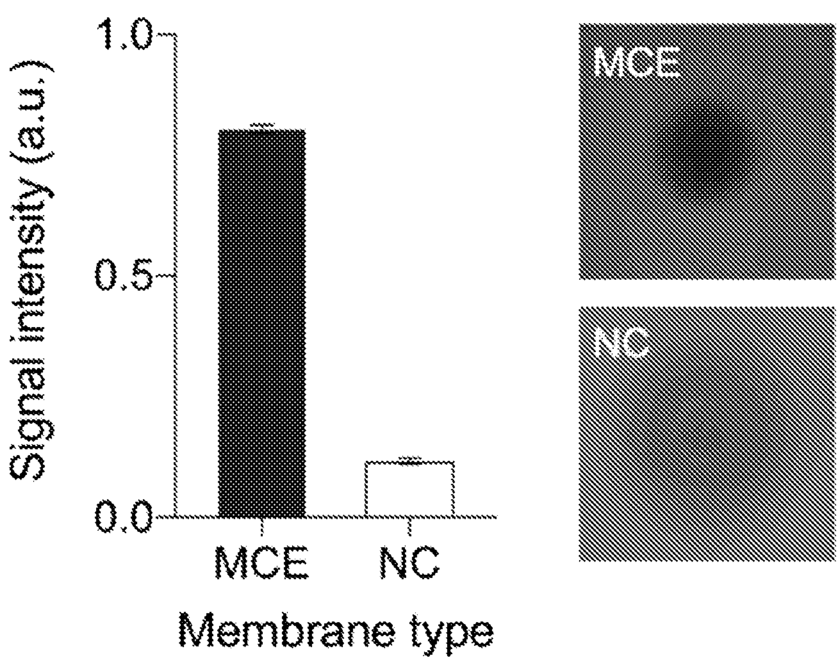
FIG. 9 is a graph comparing analytical signal from different membrane types and an image showing raw signals. Mixed cellulose esters (MCE) and nitrocellulose (NC) membranes were spotted with $THC_{BSA}$, and AuNPs conjugated with THC antibodies were introduced. The MCE sensor produced dense and strong signal, which generally improves assay's dynamic range and sensitivity. Note that the MCE membrane had both a higher protein binding capacity (~300 μm/cm$^2$) and a slower flow rate (7.411 L/min) than the commercially-available NC membrane with the lowest flow rate (25.2 μL/min; FF170HP, GE healthcare). With these traits, the MCE membrane enabled $THC_{BSA}$ immobilization in a tighter spot and also enhanced AuNP interactions with $THC_{BSA}$. Data in the bar graph were from technical triplicates and shown as mean±SD.
Figure 10:
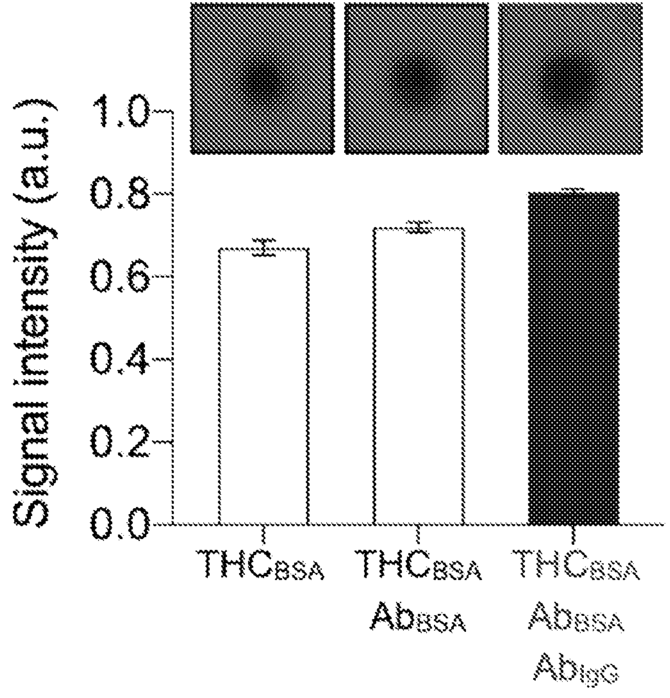
FIG. 10 is a graph of signal intensity from three different capture probe immobilization methods and an image showing raw signals. Three different methods for $THC_{BSA}$ immobilization on a MCE membrane were compared: i) direct $THC_{BSA}$ spotting; ii) BSA-antibody ($Ab_{BSA}$) capturing $THC_{BSA}$; and iii) IgG antibody ($Ab_{IgG}$) capturing $Ab_{BSA}$-$THC_{BSA}$ complexes. Equal amount of AuNPs conjugated with THC antibodies were introduced to these spots. $THC_{BSA}/Ab_{BSA}/Ab_{IgG}$ structure produced the strongest signal. Data were from technical triplicates and displayed as mean±SD.

Assay kinetics inside the membrane were analyzed. Securely immobilizing binding competitor ($THC_{BSA}$) at the membrane center was shown to enhance overall $AuNP_{Ab}$ binding efficiency, thereby producing high optical signal. The conventional approach of directly spotting $THC_{BSA}$ on a membrane, however, resulted in diffusive smaller signal spots, likely due to the loss of $THC_{BSA}$ during immobilization. Increasing the effective molecular weight of $THC_{BSA}$ was found to be effective: anti-IgG antibodies were mixed with anti-BSA antibodies and then $THC_{BSA}$ was added (FIG. 3A inset). This configuration produced the highest signal (FIG. 9). As for a membrane type, membranes of different materials (e.g., nitrocellulose, polytetrafluoroethylene, polyvinylidene fluoride, mixed cellulose ester) were tested, and their assay compatibility and product reliability were evaluated. mixed cellulose ester (MCE) were selected over the more commonly used nitrocellulose because MCE membranes produced more consistent and higher signals (FIG. 10) and were available from multiple commercial vendors.

Example 3: Read-Out Region Design

Figure 3B:
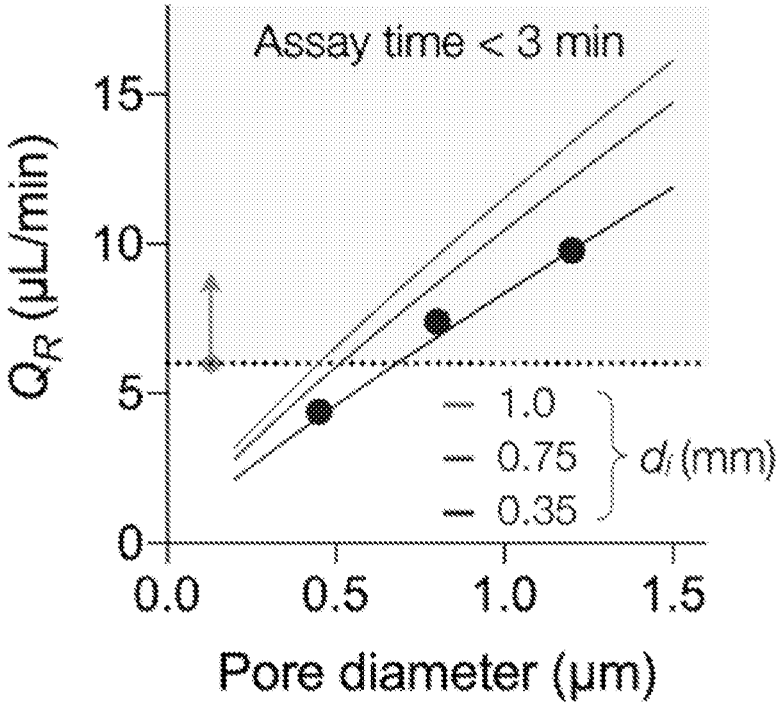
FIG. 3B is a graph showing characterization of flow rate ($Q_R$) in a radial sensor. Fluidic modeling (solid lines) predicted $Q_R$ was linearly proportional to the membrane pore diameter ($d_p$), which matched with experimental observations (solid dots). To meet a given assay speed ($Q_R$>6 μL/min; shaded region), the pore size should be larger than a threshold value, for example, $d_p \geq 0.6$ μm when $d_i=0.35$ mm. Experimental data are displayed as mean±SD from quadruplicate measurements.
Figure 11A:
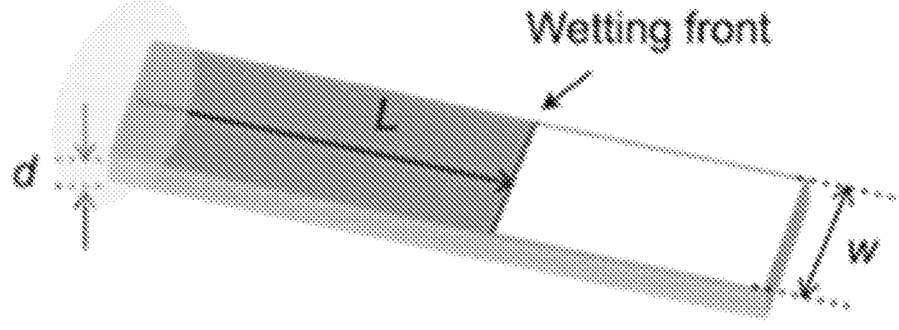
FIG. 11A is a schematic of the membrane configuration in a conventional lateral flow device format. The wetting front linearly moves along the strip direction.
Figure 11B:
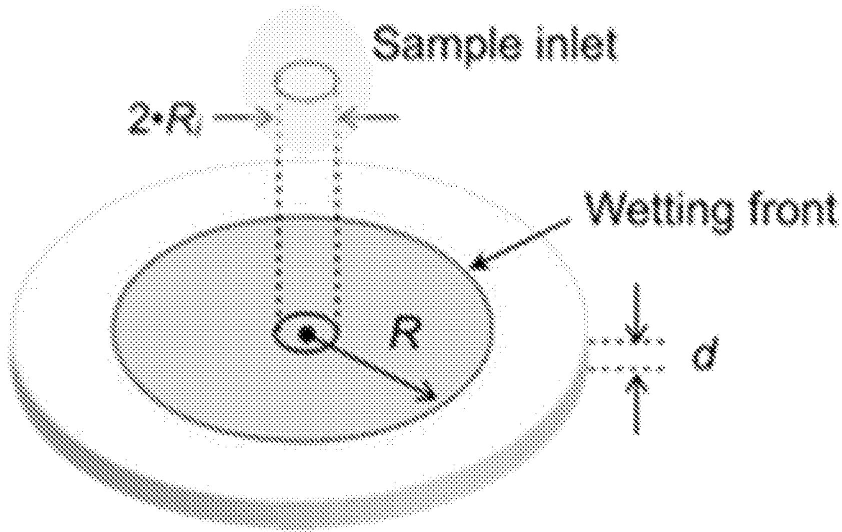
FIG. 11B is a schematic of the membrane configuration in EPOCH's disk format. The wetting front radially expands. The blue shades indicate sample reservoirs.

To guide the design of the read-out region, the fluidic behavior in porous membranes was modeled (FIGS. 11A-11B). Comparing different geometries, it was found that the disk shape supports higher fluidic flow than conventional narrow strips (FIGS. 12A-12B); the wetting front, where the capillary force drives fluids, radially expands in the disk shape, but remains the same in a strip design. The overall flow rate ($Q_R$) in the disk increased with the inlet size ($d_i$). More interestingly, $Q_R$ was expected to linearly proportional to the membrane pore size, which matched with experimental observations (FIG. 3B). These results facilitated defining the minimal pore size to meet the given assay speed. For example, to achieve the assay time of <3 min (or $Q_R$>6 μL/min), the minimum pore size was 0.6 μm with the inlet size $d_i$=0.35 mm (shaded region in FIG. 3B).

In finalizing the design, the balance between assay speed and reaction time was next considered: using large-pore membranes supports higher flow (faster assay), but increases the risk of AuNPs' exit before binding (lower sensitivity).

Figure 3C:
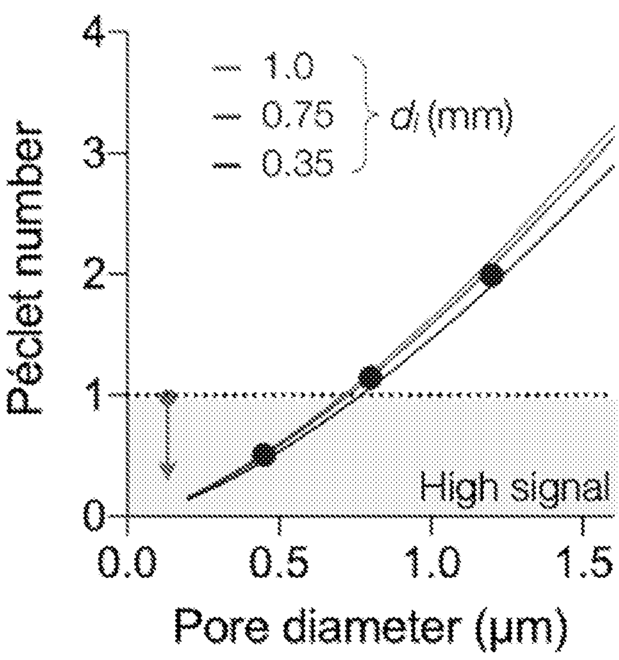
FIG. 3C is a graph showing estimation of Péclet number ($P_e$=[advection time]/[diffusion time]) of AuNPs inside the membrane sensor. Low $P_e$(<1; shaded region) was favorable to ensure efficient AuNP capture in the membrane. This requirement set the upper bound on $d_p$(≤1 μm). Combined with the lower limit from FIG. 3B, the optimal pore range was 0.6 μm≤$d_p$≤1 μm (for $d_i$=0.35 mm). Solid dots were from experimental observations (quadruplicates, mean±SD).
Figure 3D:
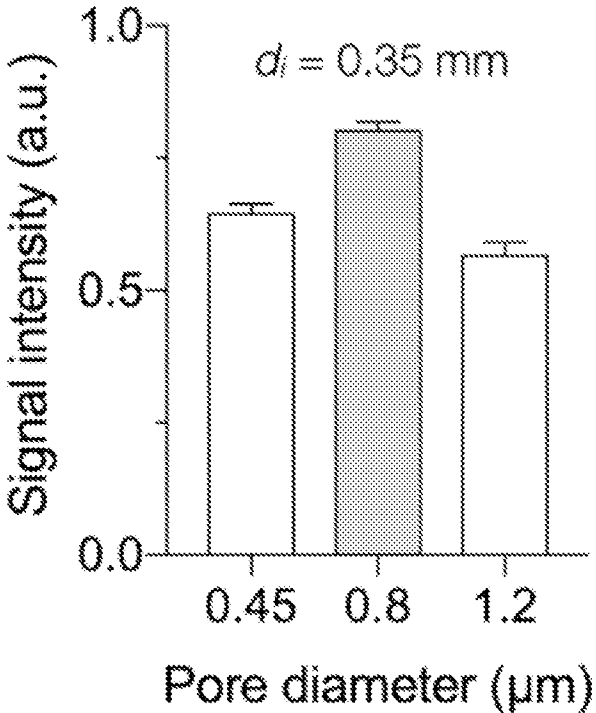
FIG. 3D is a graph showing optical signals obtained using commercial membranes with different pore sizes configured to capture AuNPs. The 0.8-μm membrane generated the highest signal as expected from FIG. 3C. The inlet diameter was fixed to 0.35 μm. Data are shown as mean±SD from quadruple measurements.

Improving AuNP-binding rates thus favored using small-pore membrane, which was equivalent to keeping low Péclet number (Pe=[diffusive transport time]/[advective transport time]; FIG. 3C). Combining these criteria, namely, $Q_R>6$ μL/min and Pe<1, determined the optimal pore range (0.5 to 1.2 μm) for a given inlet diameter. Among commercially available membranes, we chose a 0.8-μm pore MCE membrane and set $d_i=0.35$ mm for the lowest Pe. At a fixed assay time (3 min), the 0.8 μm membrane sensor indeed showed the highest signal intensity.

Example 4: Detection Method

Figure 3E:
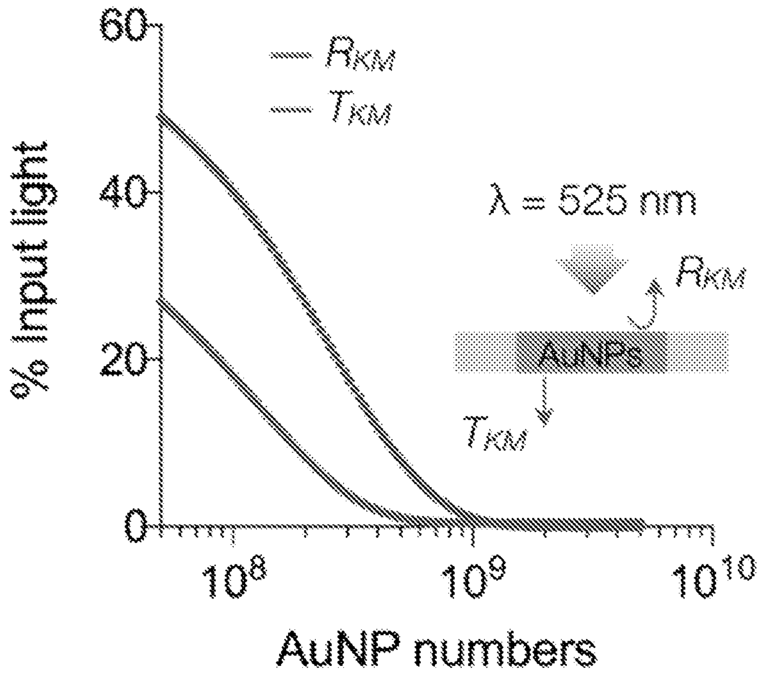
FIG. 3E is a graph showing AuNP signal from two detection modes (reflection and transmission) simulated according to Kubelka—Munk (KM) theory. Under the EPOCH experiment condition (525 nm illumination), light transmittance ($T_{KM}$) would be higher than reflectance ($R_{KM}$). Transmission mode thus had a wider detection range for varying AuNP numbers.
Figure 3F:
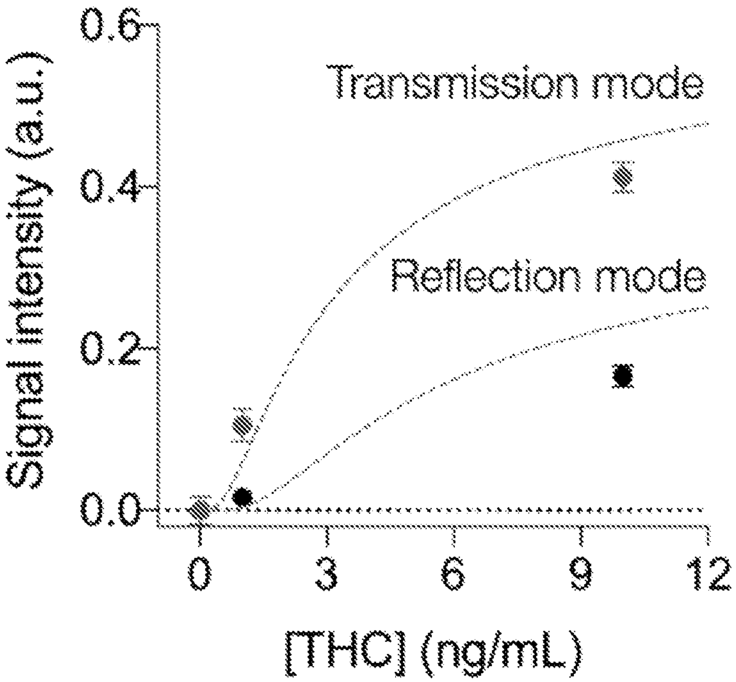
FIG. 3F is a graph showing signal levels measured either by transmission or reflection modes. The input samples contained varying amounts of THC mixed with AuNPs, which changed the number of AuNPs bound on the membrane. Note the higher analytical signal by the transmission mode detection. Solid dots represent mean±SD from technical triplicates; dashed lines are from KM simulation.

Light absorption by immobilized AuNPs (λ=524 nm) on the membrane was investigated in reflection and transmission mode. Signal level was estimated from each mode by applying Kubleka-Munk theory of light propagation in turbid media (FIGS. 13A-13B)[20,21]. The model predicted that the transmission mode produces larger signal changes with varying AuNP concentrations (FIG. 3E), which is primarily due to the enhanced light transmittance through a wet membrane[22]. Experimental data confirmed this prediction (FIG. 3F) with the transmission mode achieving higher sensitivity and resolution (FIG. 3F). These results demonstrated use of a device that could be operated in transmission optics using a smartphone camera for read-out.

Example 5: EPOCH Assay Characterization

Figure 4A:
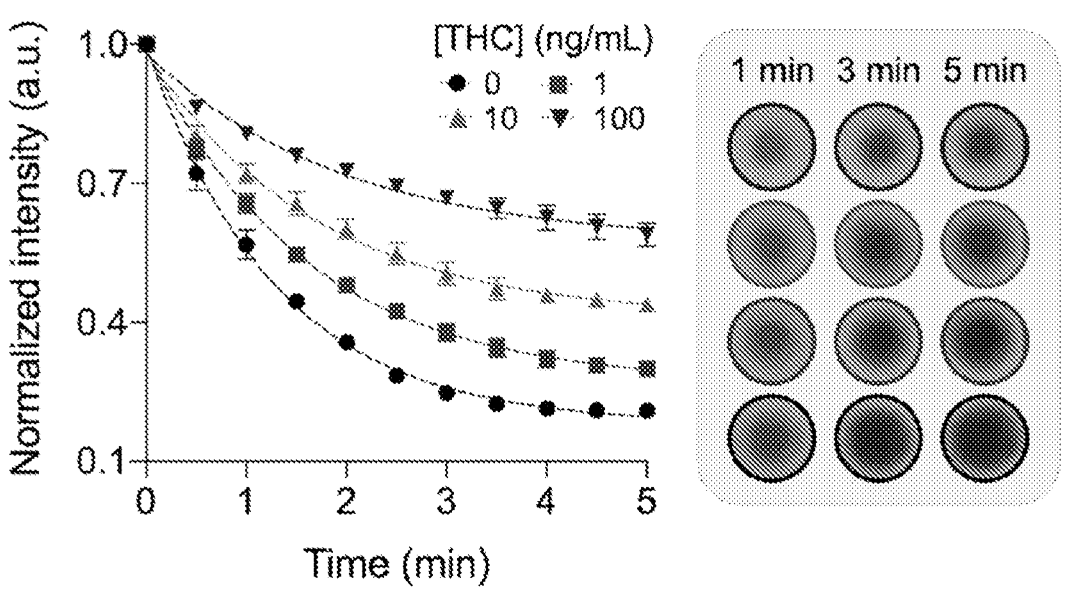
FIG. 4A is a graph showing temporal signal changes measured at different THC concentrations and an image showing AuNP binding spots. The assay followed first-order Langmuir kinetics.
Figure 15A:
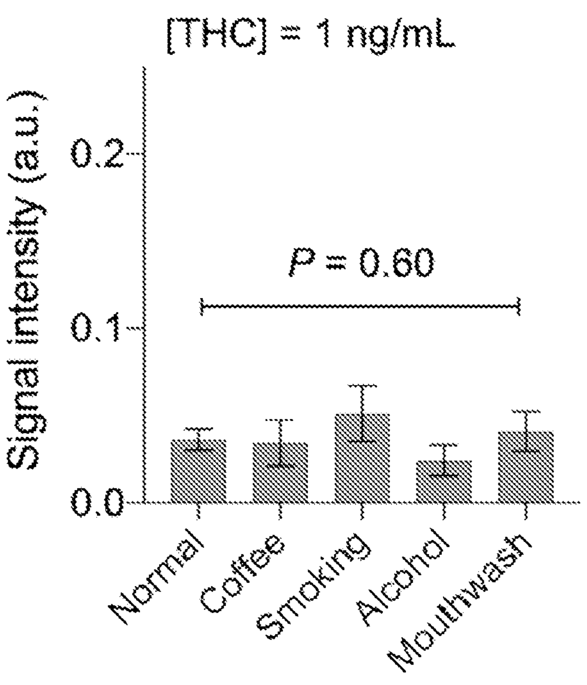
FIGS. 15A-15B are graphs of EPOCH results from saliva samples collected immediately after routine activities and spiked with known amount of THC. For a given THC concentration, the EPOCH assay reported statistically identical results (one-way ANOVA) regardless of saliva types: P=0.60, [THC]=1 ng/mL (FIG. 15A); P=0.25, [THC]=10 ng/mL (FIG. 15B). Data were from technical triplicates and shown as mean±SD.
Figure 15B:
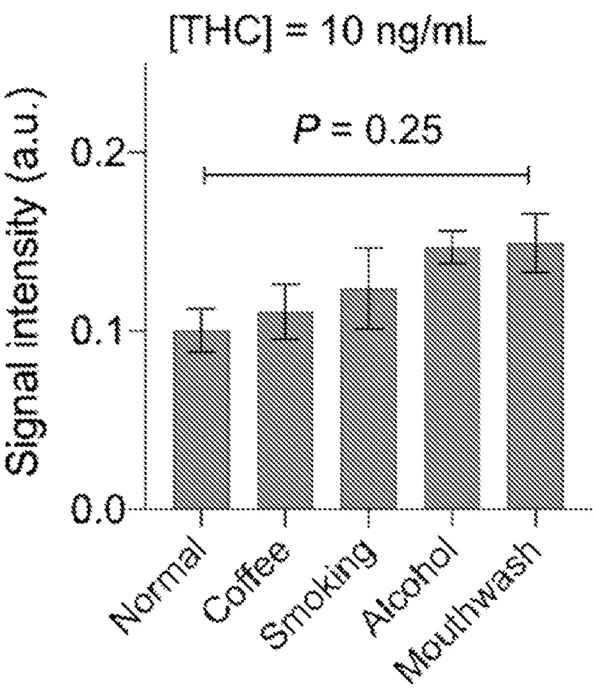

Binding kinetics between $AuNP_{Ab}$ and its intended targets, THC and THCBSA, was determined using isothermal titration calorimetry (FIG. 15). The measured association constant between THC and $AuNP_{Ab}$ was $K_a=0.074\ nM^{-1}$. A similar value was observed ($K_a=0.073\ nM^{-1}$) between $THC_{BSA}$ and $AuNP_{Ab}$. These results support the use of $THC_{BSA}$ as an equivalent competitor to THC in the assay design. Under the EPOCH assay condition, temporal signal evolution with $AuNP_{Ab}$ binding on the membrane showed first-order Langmuir adsorption kinetics (FIG. 4A). Importantly, the EPOCH assay approached the equilibrium much faster than conventional ELISA; using the porous membrane effectively enhanced AuNPs' diffusive transport to their binding sites (i.e., shorter travel time), rendering the assay largely limited by the binding reaction alone. The reasoning was further supported by estimating the Damköhler ($D_a$) number, which measures the ratio between reaction and mass-transport rates[24]. For the EPOCH assay, $D_a$ was ~0.06, indicating that diffusive transport was not a limiting factor in EPOCH.

Figure 4B:
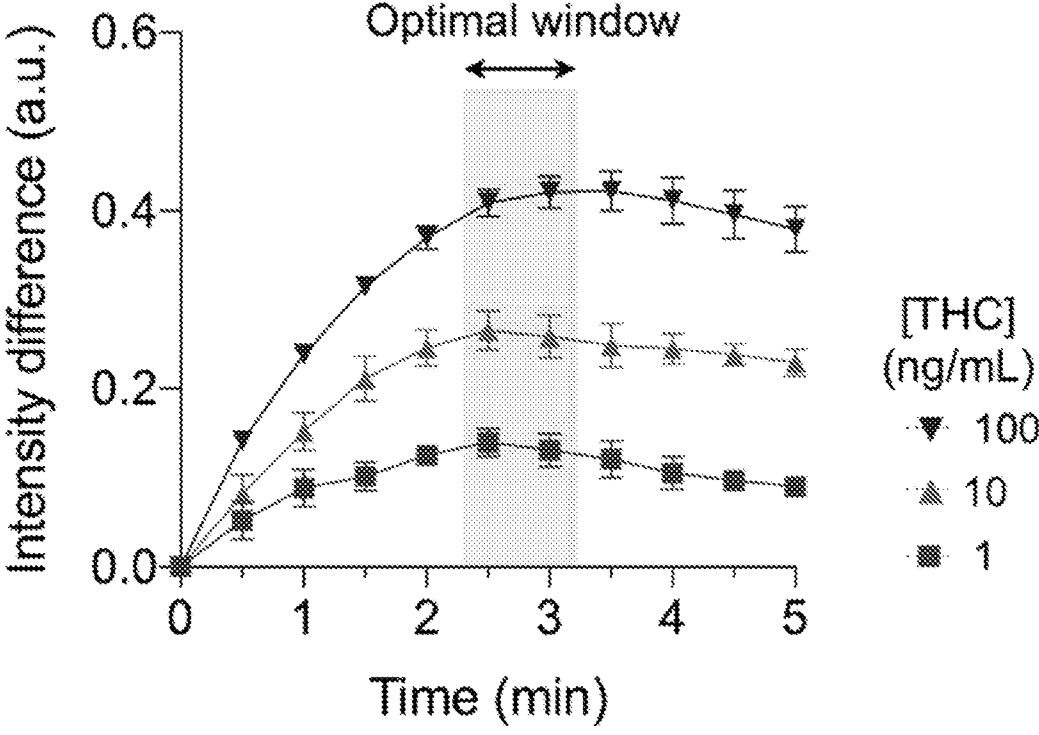
FIG. 4B is a graph showing net signal differences between THC-positive and control (no THC) samples. High signal contrast was observed around 3 min after the assay start. Accordingly, the timing for the EPOCH image acquisition was set at 3 min after sample loading.
Figure 4C:
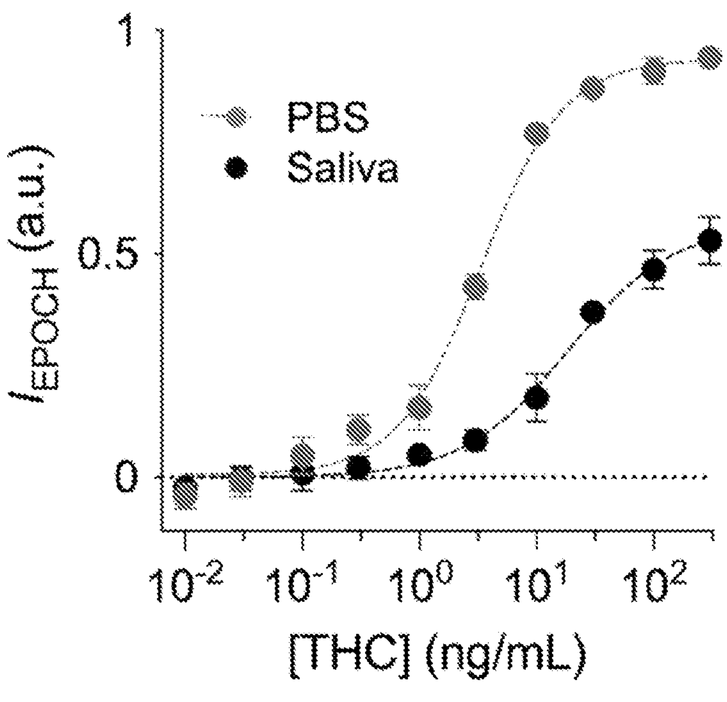
FIG. 4C is a graph showing EPOCH results from samples prepared by adding varying amounts of THC in a phosphate-buffered saline (PBS) buffer or saliva. The limits of detection were 0.12 (PBS) and 0.17 (saliva) ng/mL, and the dynamic ranges spanned about 3 orders of magnitude.
Figure 4D:
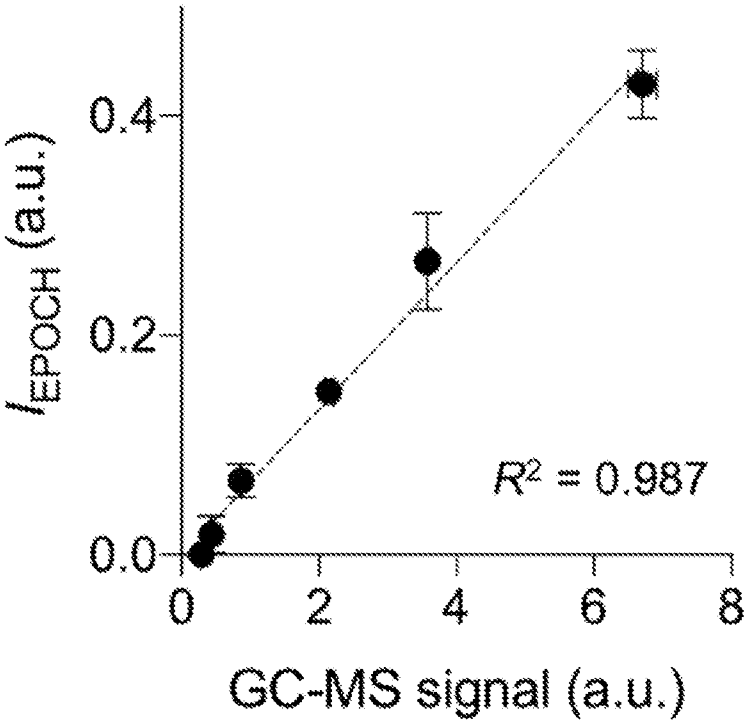
FIG. 4D is a graph showing EPOCH results compared with gold standard gas chromatography-mass spectrometry (GC-MS). EPOCH results matched well with those from GC-MS ($R^2$=0.987). Note that the EPOCH assay (3 min) was much faster than GC-MS (30 min).
Figure 14:
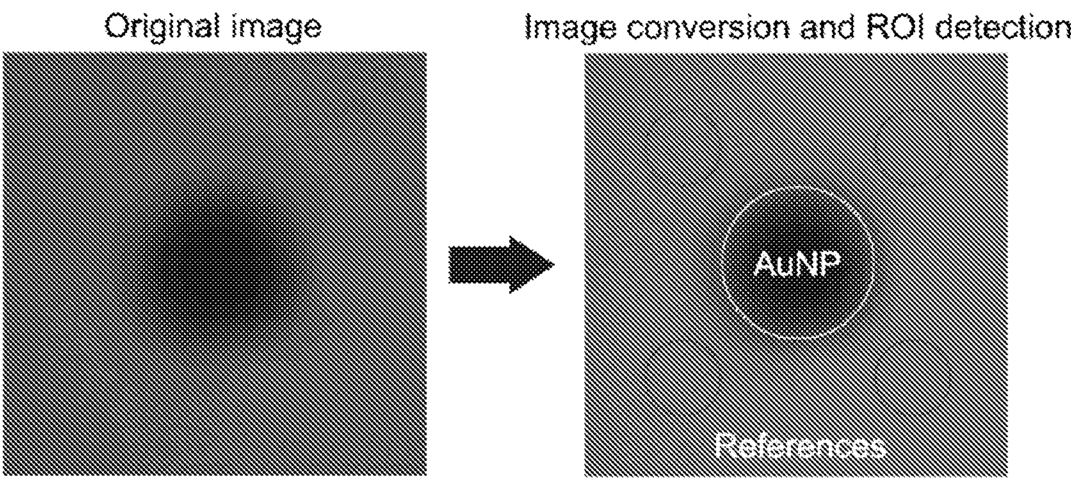
FIG. 14 are images showing EPOCH signal processing. The custom-designed smartphone app converted the acquired image into a grayscale and automatically identified regions of interest (ROIs), one for AuNPs (white circle) and four for background references (gray circles). The total area of reference ROIs is the same as that of the AuNP ROI. The EPOCH analytical metric was defined as $I_{EPOCH}=(I_{REF}-I_{AuNP})/I_{REF}$, where $I_{REF}$ and $I_{AuNP}$ were total intensities from reference ROIs and the AuNP ROI, respectively.

For a given sample, two signals were measured in the sensor cartridge, one from the THC test spot and one from a control spot. The control signal, detected by naked eyes, was to validate the successful loading of AuNP-saliva mixture on the membrane, whereas the test spot was imaged by a phone camera and automatically analyzed by a custom-designed app (FIG. 14). The EPOCH signal ($I_{EPOCH}$) was defined as the relative intensity change induced by THC-aggregated AuNPs against the membrane background (Methods for details). Time-course $I_{EPOCH}$ revealed that assay's resolving power reached its maximum around 3 min after assay start (FIG. 4B); accordingly the detection window was set to 3 min after sample injection. Applying these protocols, a THC-dilution series in pure buffer or saliva was analyzed (FIG. 4C). EPOCH assay showed the limit of detection of 0.12 ng/mL (buffer) and 0.17 ng/mL (saliva), all lower than the regulatory guideline of 1 ng/mL. The assay was quantitative, with a dynamic range spanning about 4 orders of magnitude (FIG. 4C). EPOCH's analytical results matched those of the gold standard, GC-MS (FIG. 4D). The EPOCH assay, however, was faster (5 min vs. hours), equipment-free, and performed without extensive sample preparations (see Methods for GCMS sample preparation).

Figures 4E, 5A:
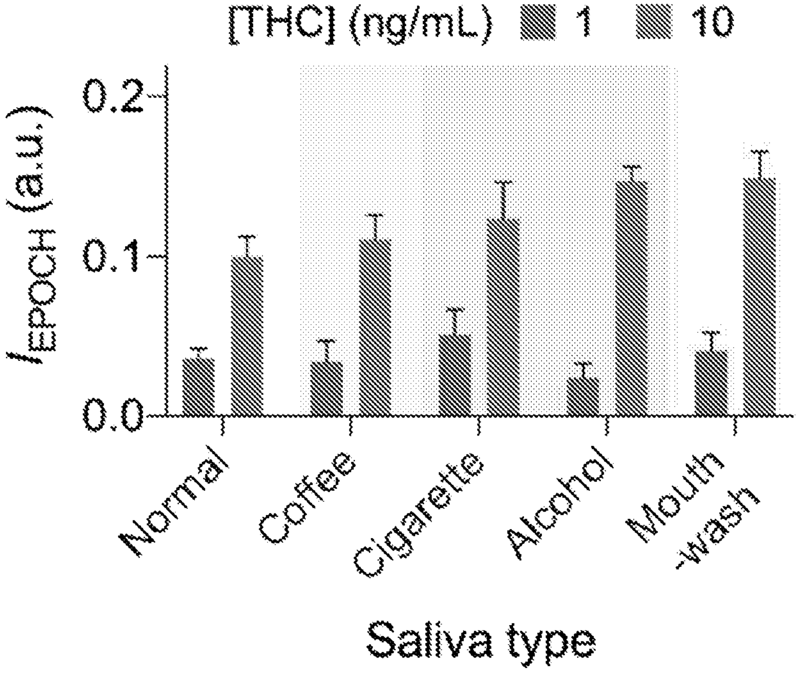
FIG. 4E is a graph showing EPOCH results from saliva samples collected after activities that affected oral cavity environment: coffee consumption, cigarette smoking, beer drinking, and rinsing with mouthwash. For a given THC concentration, EPOCH test produced statistically identical results regardless of saliva types. All data were obtained from technical triplicate measurements and displayed as mean±SD.
FIG. 5A is a graph showing analysis of oral fluid samples from 43 *cannabis* users (40 *cannabis* smokers and three persons who ate THC-infused jellies) shortly after they consumed *cannabis*. As a control, 43 oral fluid samples from volunteers with no history of *cannabis* use we tested; thirteen of them were traditional tobacco smokers and the rest were non-smokers. All *cannabis*-user samples showed high THC concentration above the regulatory guideline (1 ng/mL [THC]). Data are displayed as mean±SD from triplicate measurements.

Further, investigated how potential confounding variables such as coffee drinking, cigarette smoking, beer consumption, rinsing with mouth-wash affect signal. To compare samples, non-*cannabis* users were asked for saliva samples immediately after these activities and spiked them with two different THC doses (1 and 10 ng/mL). EPOCH tests were found to be robust in these different saliva samples (FIG. 4E). The measured signal was significantly different (P=0.0011, two-sided t-test) from background even at low THC dose (1 ng/mL). But at a given THC concentration, the signals among different saliva types were statistically identical (FIG. 15).

Example 6: Detecting THC in *Cannabis* Users

Figure 5B:
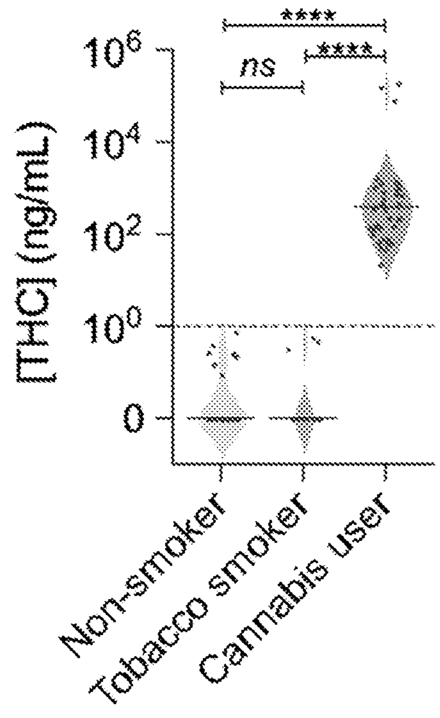
FIG. 5B is a graph showing the oral THC concentration was significantly higher in *cannabis* users than in controls (*P<0.001, Dunn's multiple comparison test), whereas THC levels were statistically identical between control groups (P>0.99, Dunn's multiple comparison test). ns, non-significant.
Figure 5C:
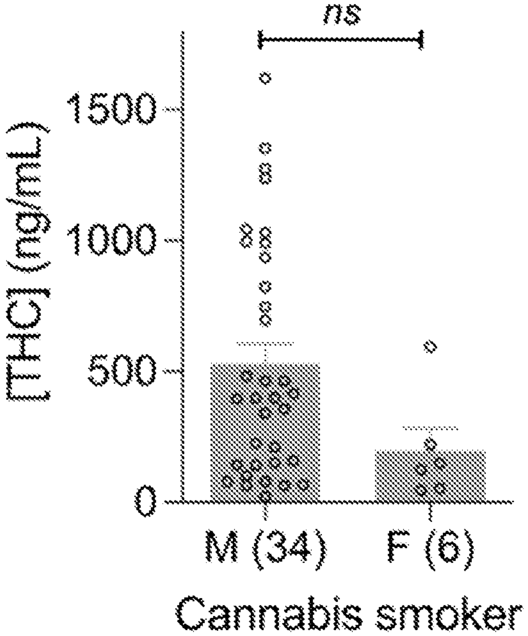
FIG. 5C is a graph showing that no significant difference in THC levels (two-sided Mann-Whitney test) were observed among male (M) and female (F) cohorts. Each data point represents a mean value from triplicate measurements.

Next, EPOCH was used for onsite THC detection. Oral fluid samples from recreational *cannabis* users (40 *cannabis* smokers and three THC jelly users) were collected within 10 minutes of product consumption and then tested. As a control, oral fluid samples were also assessed from non-*cannabis* users (13 traditional tobacco smokers and 30 non-smokers) without a history of *cannabis* use. In all *cannabis*-user samples, the EPOCH tests detected oral THC in concentrations that far exceeded the recommended guideline of 1 ng/mL (FIG. 5A); the average oral THC concentration was found to be 478 ng/mL for *cannabis* smokers and 138 μg/mL for jelly consumers. Oral THC levels of *cannabis* users were significantly higher than those of conventional tobacco smokers and non-smokers (all P<0.001, Dunn's multiple comparison test), whereas THC levels of the latter two control groups were not significantly different (P>0.99, Dunn's multiple comparison test; FIG. 5B). We observed no significant difference between male and female subjects in any of the cohorts (P>0.05, two-sided Mann-Whitney test; FIG. 5C).

Figure 5D:
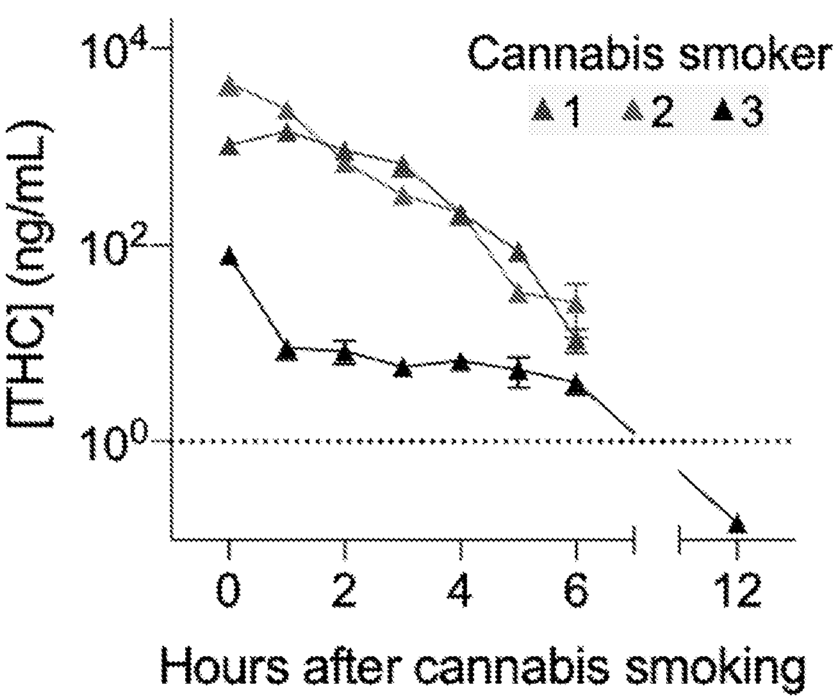
FIG. 5D is a graph showing EPOCH results from saliva samples from three *cannabis* users that were collected every hour after *cannabis* smoking, and then subjected to EPOCH testing. Salivary THC concentrations rapidly decreased over time and were expected to fall below the DRUID threshold (dotted line) within 12 hours of *cannabis* smoking.
Figure 5E:
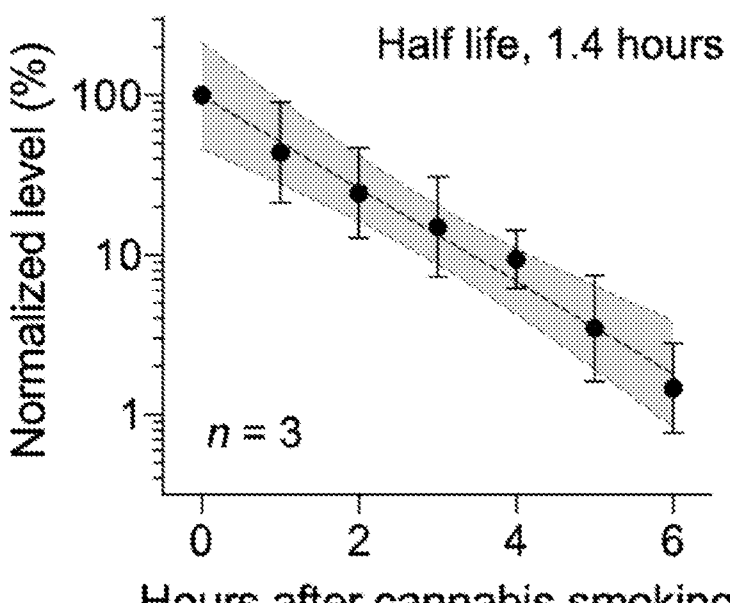
FIG. 5E is a graph showing that temporal changes in THC concentrations displayed a single-phase exponential decay (R2=0.995) with the half-life of 1.4 hour. The shade area indicates a 95% confidence band. THC concentrations were normalized against the initial value for each user. Data from three users are displayed as mean±SD.

We also monitored how THC levels changed over time after *cannabis* smoking. In this case, oral fluid samples were collected hourly after the inhalation and subjected to the EPOCH tests. We observed that oral THC levels rapidly decreased (FIG. 5D), although the values were still >1 ng/mL six hours after smoking. The estimated the half-life of THC in saliva to be about 1.4 hours (FIG. 5E), in agreement with GC-MS measurements[25,26]. Combined with the initial THC average concentration (478 ng/mL), the decay kinetics indicated that oral THC levels likely stay above 1 ng/mL in the first 12 hours after *cannabis* smoking.

Example 7: Flow in Porous Media

In this example, the fluidic flow in a membrane with two presentative geometries (a linear strip and a radial disk) was compared. An analytical model for each shape was derived. The focus was on obtaining the volume flow rate.

The following symbols are used in this example:

| | Description | SI unit | Value | Reference |
|---|---|---|---|---|
| d | membrane thickness | m | $1.6 \times 10^{-4}$ | |
| w | width of a linear membrane strip | m | | |

-continued

| | Description | SI unit | Value | Reference |
|---|---|---|---|---|
| $r_p$ | nominal radius of membrane pore | m | | |
| μ | water viscosity at 20° C. | kg/m/s | $1.002 \times 10^{-3}$ | |
| θ | contact angle of water inside the membrane pore | rad | 1.45 (=83°) | Ref. 38 |
| t | time | s | | |
| $Q_L$ | volume flow rate (linear membrane) | $m^3/s$ | | |
| $Q_R$ | volume flow rate (radial membrane) | $m^3/s$ | | |
| P | pressure | $N/m^2$ | | |
| R | wetting radius | m | | |
| Ri | inlet radius | m | | |
| K | permeability | $m^2$ | | |
| φ | porosity | | 0.82 | Manufacturer |
| $v_r$ | radial velocity of fluid in the disk membrane | m/s | | |
| γ | surface tension | N/m | 0.073 | |

1. Linear Membrane Strip

For a conventional membrane strip (FIG. 11A), the wetting distance can be estimated using the Lucas-Washburn model[39]

$$L^2 = \frac{\gamma\cos(\theta)}{2\mu} rp \cdot t. \quad [1]$$

For a strip of width w, the volume flow rate [$Q_L$=d·w·dL/dt] is then given as $$Q_L = \sqrt{\frac{\gamma\cos(\theta)}{2\mu}} \cdot \frac{w \cdot d}{2\sqrt{t}} \cdot \sqrt{r_p}. \quad [2]$$

2. Radial Membrane Disk

Next, a radial flow in a flat disk geometry (FIG. 11B) was considered. In cylindrical coordinates, the governing Navier-Stokes equation is written as $$p\left[\frac{dv_r}{dt} + v_r\frac{dv_r}{dr}\right] = -\frac{dp}{dr} - \underbrace{\frac{\mu\phi}{K}v_r}_{A}, \quad [3]$$

where (A) is the Darcy's term describing the viscous momentum transport in a porous media. In a flow with low Reynold numbers, the inertia terms in Eq. [3] can be ignored, which gives $$\frac{dp}{dr} + \frac{\mu\phi}{K}v_r = 0. \quad [4]$$

Integrating over r, Eq. [4] becomes $$\int_{pi}^{p} dp = -\frac{\mu\phi}{K}\int_{Ri}^{R} v_r dr, \quad [5]$$

where p and pi are the pressure at the radial location of R and Ri (inlet), respectively. From the mass balance requirement (i.e., conservation of total flux), we obtain an additional relation $$v_r r = R\frac{dR}{dt}. \quad [6]$$

Substituting $v_r$ in Eq. [5] with Eq. [6] and performing the integration, we get $$\Delta p = p - p_i = -\frac{\mu\phi}{K}\int_{Ri}^{R}\frac{1}{r}drR\frac{dR}{dt} = -\frac{\mu\phi}{K}\ln\left(\frac{R}{Ri}\right)R\frac{dR}{dt}. \quad [7]$$

The pressure Δp, which drives the fluidic motion, arises from the surface tension inside the pores (pore radius, rp)

$$\Delta p = -\frac{2\gamma\cos\theta}{r_p}. \quad [8]$$

Eq. 7 is further simplified by normalizing R with the characteristic length $R_i$ as s=R/$R_i$. The rearranged equation is $$\underbrace{\frac{2\gamma\cos\phi}{r_p} \cdot \frac{K}{\mu\phi R_i^2}}_{\alpha} - s\frac{d_s}{d_t}\ln s = 0. \quad [9]$$

Eq. 9 can be solved through the separation of variable, noting that s=1 at t=0.

$$t = \frac{1}{4\alpha}s^2\{\ln s^2 + s^2 - 1\} \Rightarrow \frac{4\alpha t - 1}{e} = \frac{s^2}{e}\ln\frac{s^2}{e}. \quad [10]$$

The Lambert W function can be used to inverse Eq. 10 and solve s in terms of t, $$s = (4\alpha t - 1)^{1/2}[W\left(\frac{4\alpha t - 1}{e}\right)]^{-1/2}, \quad [11]$$

where we use the relationship: y=xln x⇔x=y/W(y). Restoring R(=s·$R_i$), the temporal evolution of the radial front is written as $$R = R_i \cdot (4\alpha t - 1)^{1/2}[W\left(\frac{4\alpha t - 1}{e}\right)]^{-1/2} \quad [12]$$

where $$\alpha = \frac{2\gamma\cos\theta}{r_p} \cdot \frac{K}{\mu\phi R_i^2}. \quad [13]$$

Using Eqs. [7] and [12], we can express the radial velocity in terms of R $$v_r\left(=\frac{dR}{dt}\right) = \frac{\alpha R_i}{(R/R_i)\ln(R/R_i)}. \quad [14]$$

The radial volume flow rate is then $$Q_R = 2\pi R \cdot d \cdot v_r = 2\pi R \cdot d \cdot \frac{\alpha R_i}{(R/R_i)\ln(R/R_i)} = \frac{4\pi\gamma\cos\theta}{\mu} \cdot \frac{d}{\ln(R/R_i)} \cdot \frac{K}{\phi \cdot r_p}. \quad [15]$$

By approximating membrane pores as a tube bundle, the permeability is linked to the porosity and the pore size $$K = \frac{\phi}{8} r_p^2. \quad [16]$$

Finally, Eq. [15] is written as $$Q_R = \frac{\pi\gamma\cos\theta}{2\mu} \cdot \frac{d}{\ln(R/R_i)} \cdot r_p. \quad [17]$$

3. Comparison Between Linear and Radial Configurations

Figure 12A:
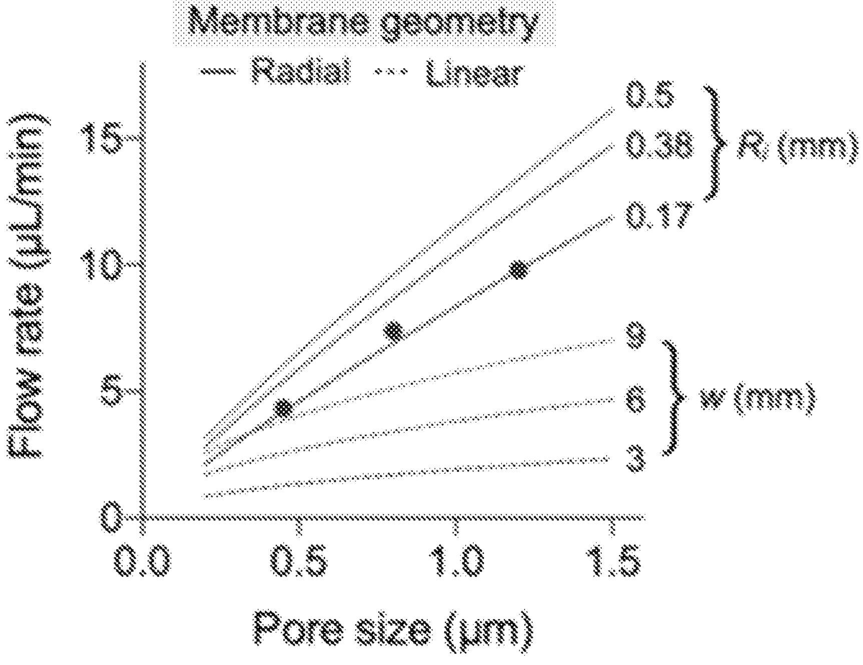
FIG. 12A is a graph of calculated flow rate (Q) at varying pore size ($r_p$). Note the different scaling: $Q \sim r_p$ (radial membrane; solid line) vs. $Q \sim r_p^{0.5}$ (linear membrane; dotted line). The following conditions were fixed: membrane thickness, 150 μm; wicking time, 3 min. Dots are measured values.
Figure 12B:
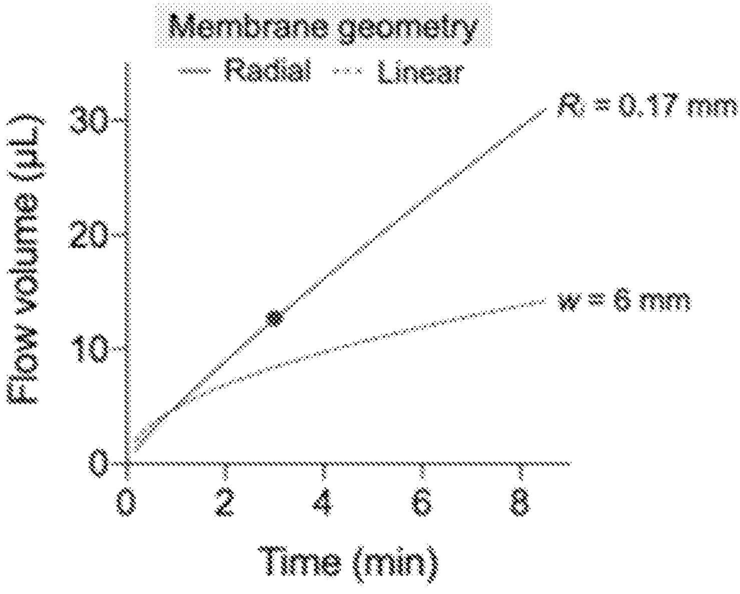
FIG. 12B is a graph of wicked flow volume as a function of time. Fluid absorption is more efficient in the radial geometry than in the linear one. The following parameters were used: nominal pore size, 0.45 μm; membrane thickness, 150 μm. The dot represents a measured value.

The following findings from this model are noted. First, the volume flow rate in the radial geometry ($Q_R$) is close to a linear function of the pore radius ($r_p$). Although $r_p$ can affect $Q_R$ through R (see Eq. 12), this effect is weak due to $Q_R$'s logarithm dependence on R. In comparison, the flow rate in the linear strip ($Q_L$) scales as $r_p^{1/2}$. Increasing the pore size, therefore, have larger impact on the flow rate in the disk geometry (FIGS. 12A-12B). Next, for a given pore size, a membrane in the radial geometry wicks more fluid than a linear strip (FIG. 12B). The capillary force at the wetting front drives the fluidic flow. This wetting front expands over time in a radial membrane, whereas it is fixed in a linear strip.

Example 8: Optical Signal Detection Mode

Figure 13A:
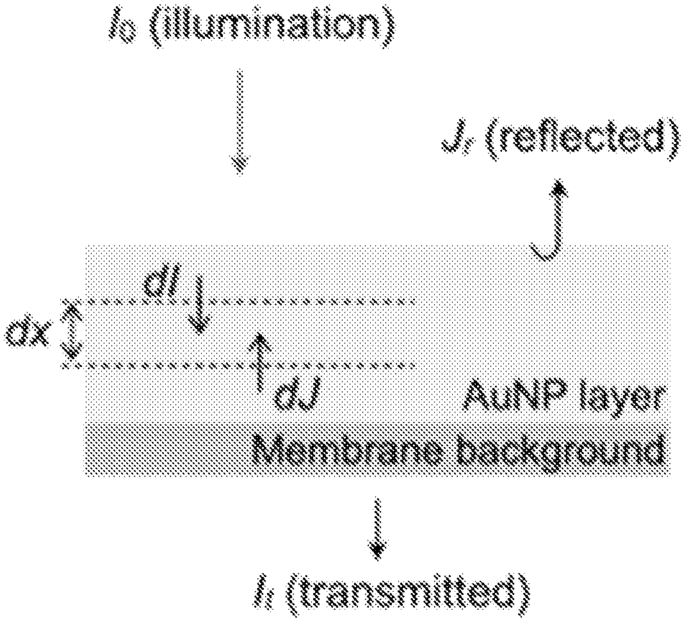
FIG. 13A is schematic of EPOCH signal modeling. Kubleka-Munk (KM) model for two light fluxes. The flux I is in the same direction of the incident light, while J is in the opposite. The detected EPOCH signal is either $R_{KM}=J_r/I_0$ (reflection mode) or $T_{KM}=I_t/I_0$ (transmission mode).
Figure 13B:
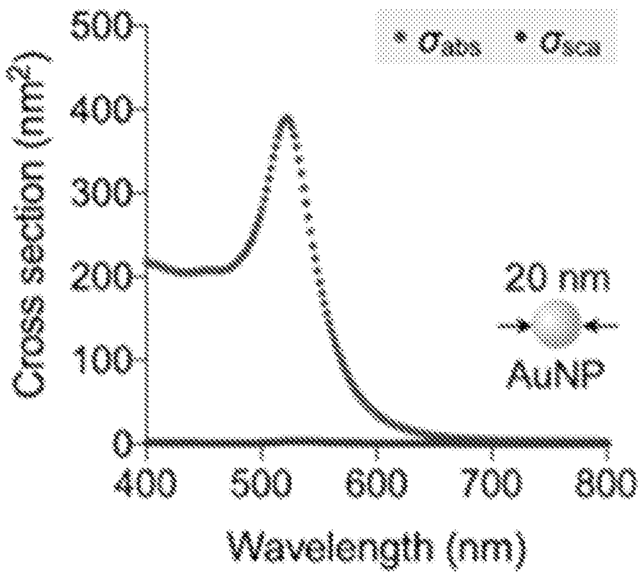
FIG. 13B is a graph of EPOCH signal modeling. Mie theory was applied to obtain a scattering ($\sigma_{sca}$) and a absorption ($\sigma_{abs}$) cross sections of a 20-nm AuNP. Plasmonic resonance is at $\lambda$=524 nm.

In this example, light propagation in a thin membrane was modeled to analyze conditions for signal detection. EPOCH's signal is generated by Au nanoparticles (AuNPs) immobilized in a membrane sheet. Kubleka-Munk (KM) theory can be applied to estimate optical properties of such diffusive light-scattering materials[40,41]. KM theory considers two light fluxes inside a material, moving towards (J) and away (I) from an illumination source (FIG. 13A).

The following symbols are used in this example:

| | Description | SI unit | Value |
|---|---|---|---|
| d | membrane thickness | m | $1.6 \times 10^{-4}$ |
| S | scattering parameter for AuNPs | 1/m | |
| K | absorption parameter for AuNPs | 1/m | |
| $R_{KM}$ | overall reflectance of membrane with AuNPs | | |
| $T_{KM}$ | overall transmittance of membrane with AuNPs | | |
| $R_g$ | reflectance of membrane only | | |
| N | AuNP numbers | | |
| V | volume of AuNPs | $m^3$ | |
| $\sigma_{abs}$ | absorption cross-section of a single AuNP | $m^2$ | |
| $\sigma_{sca}$ | scattering cross-section of a single AuNP | $m^2$ | |
| λ | incident light wavelength | nm | |

Light intensities inside the AuNP layer is described by a system of differential equations $$\begin{cases} dI = (S+K)Idx - SJdx \\ dJ = -(S+K)Jdx + SIdx \end{cases}, \quad [18]$$

where S and K are the scattering and the absorption coefficients of AuNPs. The overall reflectance ($R_{KM}=J_r/I_0$) and the transmittance ($T_{KM}=I_t/I_0$) of the material is obtained by solving Eq. (18)[40]:

$$R_{KM} = \frac{1 - R_g[a - b\coth(bSd)]}{a - R_g + b\coth(bSd)} \quad [19]$$

$$T_{KM} = \frac{b(1-R_g)}{(a-R_g)\sinh(bSd) + b\cosh(bSd)}, \quad [20]$$

where a=1+K/S and $b=(a^2-1)^{0.5}$; d is the AuNP layer thickness, which is the same as the membrane thickness in this case; $R_g$ is the background (membrane) reflectance. For monodisperse AuNPs, we can calculate S and K based on Mie theory[42]. Specifically, S and K are given as[43]

$$S = \frac{N}{V}\sigma_{sca},\ K = \frac{N}{V}\sigma_{abs}, \quad [21]$$

where N is AuNP numbers and Vis the volume occupied by AuNPs. $\sigma_{sca}$ and $\sigma_{abs}$ are the scattering and the absorption cross-sections of a single AuNP (FIG. 13B), which depend on incident light's wavelength (λ). For AuNPs used in our work (diameter, 20 nm), absorption is dominant with its maximum at $\lambda_{res}\approx 522$ nm. As an illumination source, we therefore used a light emitting diode (LED) whose wavelength (λ=525 nm) was close to $\lambda_{res}$.

The overall $R_{KM}$ and $T_{KM}$ for a given AuNP number was estimated by substituting S and K in Eqs. (19) & (20) with Eq. (21). We used following values per EPOCH device specification: d=160 μm (membrane thickness), $V=10^{-2}$ $mm^3$ (AuNP spot volume), $R_g=0.4$ (reflectance of a wet membrane filter). The results are shown in FIGS. 3E-3F. In essence, we observed that $R_{KM} \ll T_{KM}$. This can be explained from two combined effects: i) the wetted membrane has higher light transmission than dry membrane (i.e., papers become more transparent when wet)[44]; and ii) AuNPs we used have high absorption and weak scattering ($\sigma_{abs} \gg \sigma_{sca}$), which resulted in negligible reverse flux (J«1), as most back-scattered light is re-absorbed by AuNPs. Consequently, the signal decreases slowly in the transmission mode with increasing N, achieving a wider dynamic range and lower detection limit (see FIG. 3F). Based on these observations, we set the EPOCH detection condition: i) 525 nm illumination (for 20 nm AuNPs) and ii) light transmission mode.

Example 9: Reaction Kinetics Inside Membrane

In this example, reaction kinetics inside the membrane were modeled. The following symbols are used in this example:

| | Description | SI unit | Value | Note |
|---|---|---|---|---|
| d | membrane thickness | m | $1.6 \times 10^{-4}$ | |
| $r_p$ | nominal radius of membrane pore | m | $4 \times 10^{-7}$ | |
| $k_{on}$ | association rate between AuNP and $THC_{BSA}$ | $m3 \cdot s^{-1}$ | $4.1 \times 10^{-21}$ | Measured |
| $k_{off}$ | disassociation rate between AuNP and $THC_{BSA}$ | $s^{-1}$ | $5.9 \times 10^{-3}$ | Measured |
| $t_R$ | reaction time | s | | |
| $b_m$ | surface density of $THC_{BSA}$ | $m^{-2}$ | | |

-continued

| | Description | SI unit | Value | Note |
|---|---|---|---|---|
| | immobilized in the membrane | | | |
| $v_r$ | radial velocity of fluid in the disk membrane | $m \cdot s^{-1}$ | | |
| D | diffusion constant of AuNPs | $m^2 \cdot s^{-1}$ | $1.2 \times 10^{-11}$ | Ref. 45 |
| φ | porosity | | 0.82 | Manufacturer |
| $c_s$ | concentration of AuNPs near the binding site | $m^{-3}$ | | |
| $c_0$ | concentration of input AuNPs | $m^{-3}$ | | |
| $P_e$ | Péclet number (convection rate/diffusion rate) | | | |
| $D_a$ | Damköhler number (reaction rate/diffusion rate) | | | |

1. Convection Vs. Diffusion (Péclet Number)

To estimate the EPOCH assay kinetics, two physical motions of AuNPs were considered: i) advection that carries AuNPs through the porous membrane and ii) random diffusion of particles inside the pore. The porous membrane was approximated as a bundle of cylindrical channels (radius, $r_p$=400 nm). It was assumed that AuNPs, conjugated with multiple THC-antibodies, immediately bind to $THC_{BSA}$ upon encountering with them. The Péclet number, which measures the ratio of convection over diffusion, is given as $$P_e = \frac{\text{convection rate}}{\text{diffusion rate}} = \frac{v_r}{D/(2 \cdot r_p)}, \quad [22]$$

where D is the diffusion coefficient of an AuNP in water (~$1.2\times10^{-11}$ $m^2$/s). Under the EPOCH experimental condition ($v_r \approx 1.2\times10^{-5}$ m/s, $r_p$=400 nm), we obtain $P_e$~0.8.

2. Reaction Vs. Diffusion (Damköhler Number)

How fast the reaction takes place as AuNPs diffuse to the binding sites was considered. The membrane was approximated as a bundle of small pipes whose diameter is equal to the pore size ($2 \cdot r_p$). The inner surface of the pipe is immobilized with $THC_{BSA}$ that captures AuNPs (initial concentration, $c_0$). The reactive flux ($J_R$) for this binding reaction can be written as[46]

$$J_R = k_{on} c_s b_m A, \quad [23]$$

where $c_s$ is AuNP concentration near the pipe surface, $b_m$ is the surface density of $THC_{BSA}$, A is the surface area of the pipe, and $k_{on}$ is the association constant. We expect that $c_s < c_0$, because the particles bind to $THC_{BSA}$. This concentration gradient will generate diffusive flux ($J_D$):

$$J_D = D\frac{(c_0 - c_s)A}{r_p}. \quad [24]$$

In a steady state, these two fluxes are balanced, $J_R = J_D$, which leads to $$\frac{c_s}{c_0} = \left(1 + \frac{k_{on} b_m r_p}{D}\right)^{-1}. \quad [25]$$

The dimensionless entity, $Da = k_{on} b_m r_p / D$, is essentially the Damköhler number which is the ratio between reaction and diffusion rates. When $D_a < 1$ (or equivalently $c_s \approx c_0$), diffusion is fast enough to supply AuNPs to the binding sites (reaction-limited). The assay time is then essentially set by the reaction time:

$$t_R = (k_{off} + k_{on} c_0)^{-1}, \quad [26]$$

where $k_{off}$ is the dissociate rate of AuNPs from $THC_{BSA}$. From the kinetic measurements (FIG. 4A), we obtained $k_{on} = 2.5\times10^6\ M^{-1} \cdot s^{-1} (= 4.1\times10^{-21}\ m^3 \cdot s^{-1})$ and $k_{off} = 5.9\times10^{-3}\ s^{-1}$.

During the sensor construction, we immobilized about $2.2\times10^{12}$ $THC_{BSA}$ molecules in a spot whose radius $r_s$, is about 1.6 mm. The spot volume is ~1 $mm^3$ ($=\pi \cdot r_s^2 \cdot d \cdot \varphi$). Using the pipe-bundle model, this volume is equivalent to having $1.24\times10^6$ pipes (radius $r_p$=400 nm, length $L_p = r_s$=1.6 mm). The estimated $b_m$ is then $4.4\times10^{14}$ $m^{-2}$. Using these values, the Damköhler number of the EPOCH assay system is $D_a$=0.06, which implies that the assay would be reaction-limited. Typical timescale of the assay then follows Eq. 26. With $c_0$=1.16 nM used in the assay, $t_R$~114 s~2 min, which matches with experimental observation (FIG. 4A).

REFERENCES

1. Key substance use and mental health indicators in the United States: Results from the 2018 national survey on drug use and health. (2019).
2. Cavazos-Rehg, P. A., Krauss, M. J., Sowles, S. J., Floyd, G. M., Cahn, E. S., Chaitan, V. L., Ponton, M. Leveraging user perspectives for insight into *cannabis* concentrates. Am J Drug Alcohl Abuse 44(6):628-641 (2018).
3. Meier, M. H., Docherty, M., Leischow, S. J., Grimm, K. J., Pardini D. *Cannabis* concentrate use in adolescents. Pediatrics 144(3) e20190338 (2019).
4. Prashad, S. & Filbey, F. M. Cognitive motor deficits in *cannabis* users. Curr Opin Behav Sci 13, 1-7 (2017).
5. Desrosiers, N. A., Ramaekers, J. G., Chauchard, E., Gorelick, D. A. & Huestis, M. A. Smoked *cannabis*' psychomotor and neurocognitive effects in occasional and frequent smokers. J Anal Toxicol 39, 251-261 (2015).
6. Hartman, R. L. & Huestis, M. A. *Cannabis* effects on driving skills. Clin Chem 59, 478-492 (2013).
7. Fergusson, D. M., Horwood, L. J. & Boden, J. M. Is driving under the influence of *cannabis* becoming a greater risk to driver safety than drink driving? Findings from a longitudinal study. Accid. Anal. Prev. 40, 1345-1350 (2008).
8. Rogeberg, O. & Elvik, R. The effects of *cannabis* intoxication on motor vehicle collision revisited and revised. Addiction 111, 1348-1359 (2016).
9. Hartley, S., Simon, N., Larabi, A., Vaugier, I., Barbot, F., Quera-Salva, M.-A. & Alvarez, J. C. Effect of smoked *cannabis* on vigilance and accident risk using simulated driving in occasional and chronic users and the pharmacokinetic-pharmacodynamic relationship. Clin. Chem. 65, 684-693 (2019).
10. Dahlgren, M. K., Sagar, K. A., Smith, R. T., Lambros, A. M., Kuppe M. K., Gruber, S. A. Recreational *cannabis* use impairs driving performance in the absence of acute intoxication. Drug and Alcohol Dependence 208 (2020).
11. Verstraete, A. G. Detection times of drugs of abuse in blood, urine, and oral fluid. Therapeutic drug monitoring (2004).
12. Andas, H. T., Krabseth, H. M., Enger, A., Marcussen, B. N., Haneborg, A. M., Christophersen, A. S., Vindenes, V.

& Oiestad, E. L. Detection time for the in oral fluid after frequent *cannabis* smoking. Ther Drug Monit 36, 808-814 (2014).

13. Lee, D., Milman, G., Barnes, A. J., Goodwin, R. S., Hirvonen, J. & Huestis, M. A. Oral fluid cannabinoids in chronic, daily *cannabis* smokers during sustained, monitored abstinence. Clin Chem 57, 1127-1136 (2011).
14. Desrosiers, N. A., Himes, S. K., Scheidweiler, K. B., Concheiro-Guisan, M., Gorelick, D. A. & Huestis, M. A. Phase I and ii cannabinoid disposition in blood and plasma of occasional and frequent smokers following controlled smoked *cannabis*. Clin Chem 60, 631-643 (2014).
15. Anizan, S., Milman, G., Desrosiers, N., Barnes, A. J., Gorelick, D. A. & Huestis, M. A. Oral fluid cannabinoid concentrations following controlled smoked *cannabis* in chronic frequent and occasional smokers. Anal Bioanal Chem 405, 8451-8461 (2013).
16. Desrosiers, N. A. & Huestis, M. A. Oral fluid drug testing: Analytical approaches, issues and interpretation of results. J Anal Toxicol 43, 415-443 (2019).
17. Milman, G., Schwope, D. M., Gorelick, D. A. & Huestis, M. A. Cannabinoids and metabolites in expectorated oral fluid following controlled smoked *cannabis*. Clin Chim Acta 413, 765-770 (2012).
18. Bosker, W. M. & Huestis, M. A. Oral fluid testing for drugs of abuse. Clin Chem 55, 1910-1931 (2009).
19. Swortwood, M. J., Newmeyer, M. N., Andersson, M., Abulseoud, 0. A., Scheidweiler, K. B. & Huestis, M. A. Cannabinoid disposition in oral fluid after controlled smoked, vaporized, and oral *cannabis* administration. Drug Test. Anal. 9, 905-915 (2017).
20. Kubelka, P. New contributions to the optics of intensely light-scattering materials. J Opt Soc Am 38, 448-457 (1948).
21. Wang, J. X., Nilsson, A. M., Fernandes, D. L. A. & Niklasson, G. A. Angle dependent light scattering by gold nanospheres. J. Phys. Conf. Ser. 682, 012018 (2016).
22. Swanson, C., Lee, S., Aranyosi, A. J., Tien, B., Chan, C., Wong, M., Lowe, J., Jain, S. & Ghaffari, R. Rapid light transmittance measurements in paper-based microfluidic devices. Sens Biosensing Res 5, 55-61 (2015).
23. Morita, I., Oyama, H., Yasuo, M., Matsuda, K., Katagi, K., Ito, A., Tatsuda, H., Tanaka, H., Morimoto, S. & Kobayashi, N. Antibody fragments for on-site testing of cannabinoids generated via in vitro affinity maturation. Biol Pharm Bull 40, 174-181 (2017).
24. Squires, T. M., Messinger, R. J. & Manalis, S. R. Making it stick: Convection, reaction and diffusion in surface-based biosensors. Nat. Biotechnol. 26, 417-426 (2008).
25. Kauert, G. F., Ramaekers, J. G., Schneider, E., Moeller, M. R. & Toennes, S. W. Pharmacokinetic properties of 69-tetrahydrocannabinol in serum and oral fluid. J. Anal. Toxicol. 31, 288-293 (2007).
26. Toennes, S. W., Ramaekers, J. G., Theunissen, E. L., Moeller, M. R. & Kauert, G. F. Pharmacokinetic properties of δ9-tetrahydrocannabinol in oral fluid of occasional and chronic users. J. Anal. Toxicol. 34, 216-221 (2010).
27. Cerdá, M., Mauro, C., Hamilton, A., Levy, N. S., Santaella-Tenorio, J., Hasin, D., Wall, M. M., Keyes, K. M. & Martins, S. S. Association between recreational marijuana legalization in the united states and changes in marijuana use and *cannabis* use disorder from 2008 to 2016. JAMA Psychiatry (2019).
28. Milman, G., Schwope, D. M., Schwilke, E. W., Darwin, W. D., Kelly, D. L., Goodwin, R. S., Gorelick, D. A. & Huestis, M. A. Oral fluid and plasma cannabinoid ratios after around-the-clock controlled oral δ(9)-tetrahydrocannabinol administration. Clin Chem 57, 1597-1606 (2011).
29. Childs, E., Lutz, J. A. & de Wit, H. Dose-related effects of delta-9-thc on emotional responses to acute psychosocial stress. Drug Alcohol Depend 177, 136-144 (2017).
30. Drummer, O. H. Drug testing in oral fluid. Clin Biochem Rev 27, 147-159 (2006).
31. Lee, D. & Huestis, M. A. Current knowledge on cannabinoids in oral fluid. Drug Test. Anal. 6, 88-111 (2014).
32. Perez-Reyes, M. & Wall, M. E. Presence of delta9-tetrahydrocannabinol in human milk. N. Engl. J. Med. 307, 819-820 (1982).
33. Jaeger, J. Digit symbol substitution test: The case for sensitivity over specificity in neuropsychological testing. J. Clin. Psychopharmacol. 38, 513-519 (2018).
34. Pham, L., Harris, T., Varosanec, M., Kosa, P. & Bielekova, B. Smartphone-based symbol-digit modalities test reliably measures cognitive function in multiple sclerosis patients. medRxiv (2020).
35. Zhang, Z., Li, W., Zhao, Q., Cheng, M., Xu, L. & Fang, X. Highly sensitive visual detection of copper (ii) using water-soluble azide-functionalized gold nanoparticles and silver enhancement. Biosens Bioelectron 59, 40-44 (2014).
36. Yang, Y., Ozsoz, M. & Liu, G. Gold nanocage-based lateral flow immunoassay for immunoglobulin g. Mikrochim Acta 184, 2023-2029 (2017).
37. Hu, J., Wang, L., Li, F., Han, Y. L., Lin, M., Lu, T. J. & Xu, F. Oligonucleotide-linked gold nanoparticle aggregates for enhanced sensitivity in lateral flow assays. Lab Chip 13, 4352-4357 (2013).
38. Hong S, Kim W. Dynamics of water imbibition through paper channels with wax boundaries. Microfluid Nanofluid 19:845-853 (2015).
39. Gong M M, Sinton D. Turning the Page: Advancing Paper-Based Microfluidics for Broad Diagnostic Application. Chem Rev 117:8447-8480 (2017).
40. Wang J X, Nilsson A M, Fernandes D L A, Niklasson G A. Angle dependent light scattering by gold nanospheres. J Phys Conf Ser 682:012018 (2016).
41. Kubelka P. New contributions to the optics of intensely light-scattering materials. J Opt Soc Am 38:448-457 (1948).
42. Jain P K, Lee K S, El-Sayed I H, El-Sayed M A. Calculated absorption and scattering properties of gold nanoparticles of different size, shape, and composition: applications in biological imaging and biomedicine. J Phys Chem B 110:7238-7248 (2006).
43. Maheu B, Letoulouzan J N, Gouesbet G. Four-flux models to solve the scattering transfer equation in terms of Lorenz-Mie parameters. Appl Opt 23:3353 (1984).
44. Swanson C, Lee S, Aranyosi A J, Tien B, Chan C, Wong M, Lowe J, Jain S, Ghaffari R. Rapid light transmittance measurements in paper-based microfluidic devices. Sens Bio-sensing Res 5:55-61 (2015).
45. Wong K, Chen C, Wei K, Roy V A L, Chathoth S M. Diffusion of gold nanoparticles in toluene and water as seen by dynamic light scattering. J Nanopart Res 17:153 (2015).
46. Squires T M, Messinger R J, Manalis S R. Making it stick: convection, reaction and diffusion in surface-based biosensors. Nat Biotechnol 26:417-426 (2008).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A device for detecting a controlled substance, the device comprising:

(a) a sample processing module comprising:

a metering reservoir reversibly connected to a sample chamber, an air chamber, and a loading chamber via a first fluidic channel, a second fluidic channel, and a third fluidic channel, respectively, wherein the metering reservoir is reversibly connected to a waste chamber via a syphon that is configured to actuate upon a predetermined volume of liquid being received in the metering reservoir, wherein the loading chamber comprises a detection probe that binds a controlled substance, and wherein the loading chamber is connected to a fourth fluidic channel comprising one or more openings;

(b) a sensor cartridge comprising:

a control membrane aligned to the control sample outlet and comprising a loading control probe that binds to the detection probe, and a test membrane aligned to the test sample outlet and comprising a capture probe comprising the controlled substance; and (c) a first cap having a protrusion that forms a piston relative to the sample chamber when the first cap is joined to the sample chamber, and a second cap having a protrusion that forms a piston relative to the air chamber when the second cap is joined to the air chamber.

2. The device of claim 1, wherein the metering reservoir is positionable in a first position where the metering reservoir is aligned with the first fluidic channel to allow fluid to flow from the sample chamber to the metering reservoir.

3. The device of claim 1, wherein the metering reservoir is positionable in a second position where the metering reservoir is aligned with the second fluidic channel to allow air to flow from the air chamber to the metering reservoir, and where the metering reservoir is aligned with the third fluidic channel to allow fluid to flow from the metering reservoir to the loading chamber.

4. The device of claim 1, wherein the reservoir has a sample volume of 5 to 50 μL.

5. The device of claim 4, wherein the reservoir has a sample volume of 15 to 25 μL.

6. The device of claim 1, wherein the first fluidic channel comprises a filter between the sample chamber and the metering reservoir.

7. The device of claim 1, wherein the fourth fluidic channel comprises a microfluidic mixer.

8. The device of claim 1, wherein the detection probe is conjugated to a detectable label.

9. The device of claim 1, wherein the control membrane and the test membrane are disk shaped.

10. The device of claim 1, wherein the control membrane and the test membrane are laminated.

11. The device of claim 1, wherein the loading control probe and the capture probe are immobilized at the center of the control membrane and test membrane, respectively.

12. The device of claim 1, wherein the sensor cartridge is detachable from the sample processing module.

13. The device of claim 1, wherein the sensor cartridge comprises a housing.

14. The device of claim 1, wherein the sample processing module comprises circumferential screw threads, and the first cap and the second cap comprise circumferential receiving threads.

15. The device of claim 1, further comprising a detection cradle comprising a light source and a lens.

16. A method of detecting a controlled substance in a saliva sample from a subject, the method comprising:

(a) collecting a saliva sample from a subject using an oral swab, (b) loading the oral swab into the sample processing module of the device of any one of claims 1 to 15, (c) engaging the first cap with the sample chamber and the second cap with the air chamber, and (d) determining presence or absence of the controlled substance in the saliva sample based on presence or absence of a signal from the sensor cartridge.

17. The method of claim 16, wherein the controlled substance is a cannabinoid, an opioid, a stimulant, or a central nervous system (CNS) depressant.

18. The method of claim 17, wherein the cannabinoid is tetrahydrocannabinol (THC) or tetrahydrocannabivarin (THCV).

19. The method of claim 17, wherein the opioid is selected from the group consisting of codeine, fentanyl, heroin, hydrocodone, hydromorphone, morphine, and oxycodone.

20. The method of claim 17, wherein the stimulant is an amphetamine or cocaine.

21. The method of claim 20, wherein the amphetamine is selected from the group consisting of 3,4-methylenedioxymethamphetamine (MDMA), dextroamphetamine, methamphetamine, and methylphenidate.

22. The method of claim 17, wherein the CNS depressant is a barbiturate or a benzodiazepine.

23. The method of claim 16, wherein the oral swab is rolled in the mouth of the subject.

24. The method of claim 16, wherein steps (a)-(d) are performed in a total of 1 to 10 minutes.

25. The method of claim 16, further comprising loading the sensor cartridge into the detection cradle, and determining amount of the controlled substance in the saliva sample based on amount of signal detected from the sensor by a detection device positioned in the detection cradle.

26. The method of claim 25, wherein the detection device is a mobile electronic device.

27. The method of claim 26, wherein the mobile electronic device is a mobile phone or a portable computer.

* * * * *